US012807648B2

(12) United States Patent
Brown et al.

(10) Patent No.: US 12,807,648 B2
(45) Date of Patent: Nov. 24, 2026

(54) CYCLIC APELIN RECEPTOR AGONISTS

(71) Applicant: NXERA PHARMA UK LIMITED, Cambridge (GB)

(72) Inventors: Giles Albert Brown, Cambridge (GB); Miles Stuart Congreve, Cambridge (GB); Conor Scully, Cambridge (GB); Rebecca Paul, Cambridge (GB)

(73) Assignee: NXERA PHARMA UK LIMITED, Cambridge (GB)

( * ) Notice: Subject to any disclaimer, the term of this patent is extended or adjusted under 35 U.S.C. 154(b) by 711 days.

(21) Appl. No.: 18/031,571

(22) PCT Filed: Oct. 12, 2021

(86) PCT No.: PCT/GB2021/052634

§ 371 (c)(1),
(2) Date: Apr. 12, 2023

(87) PCT Pub. No.: WO2022/079426

PCT Pub. Date: Apr. 21, 2022

(65) Prior Publication Data

US 2023/0382950 A1 Nov. 30, 2023

(30) Foreign Application Priority Data

Oct. 12, 2020 (GB) ..................................... 2016149

(51) Int. Cl.
*C07K 7/08* (2006.01)
*A61K 47/54* (2017.01)

(52) U.S. Cl.
CPC .............. *C07K 7/08* (2013.01); *A61K 47/545* (2017.08)

(58) Field of Classification Search
CPC ........... C07K 7/08; C07K 7/02; A61K 47/545
See application file for complete search history.

(56) References Cited

FOREIGN PATENT DOCUMENTS

| | | | | |
|---|---|---|---|---|
| CN | 109771634 A | | 5/2019 | |
| GB | 2551945 A | | 1/2018 | |
| WO | WO 2015/147641 A1 | | 10/2015 | |
| WO | WO-2015191781 A2 | * | 12/2015 | ................ A61P 9/00 |
| WO | WO 2018/101398 A1 | | 6/2018 | |
| WO | WO 2019/005623 A1 | | 1/2019 | |

OTHER PUBLICATIONS

Hamada, Juri, et al. "Evaluation of novel cyclic analogues of apelin." International journal of molecular medicine 22.4 (2008): 547-552. (Year: 2008).*

Wysocka, Marta B., Katarzyna Pietraszek-Gremplewicz, and Dorota Nowak. "The role of apelin in cardiovascular diseases, obesity and cancer." Frontiers in physiology 9 (2018): 557. (Year: 2018).*

Antushevich, Hanna, and Maciej Wójcik. "Apelin in disease." Clinica chimica acta 483 (2018): 241-248. (Year: 2018).*

Hamada, et al. International journal of molecular medicine 22.4: 547-552 (2008)) (Year: 2008).*

Hamada, et al. International journal of molecular medicine 22.4: 547-552 (2008)) (Year: 2008) (Year: 2008).*

International Search Report for PCT/GB2021/052634 (PCT/ISA/210) mailed on Jan. 19, 2022.

International Search Report for PCT/GB2021/052636 (PCT/ISA/210) mailed on Jan. 19, 2022.

Wang et al., "Apelin protects against abdominal aortic aneurysm and the therapeutic role of neutral endopeptidase resistant apelin analogs", Proceedings of the National Academy of Sciences, vol. 116, No. 26, Jun. 12, 2019, pp. 13006-13015, total of 13 pages.

Written Opinion of the International Searching Authority for PCT/GB2021/052634 (PCT/ISA/237) mailed on Jan. 19, 2022.

Written Opinion of the International Searching Authority for PCT/GB2021/052636 (PCT/ISA/237) mailed on Jan. 19, 2022.

U.S. Office Action for U.S. Appl. No. 18/031,416, dated Mar. 17, 2026.

U.S. Office Action for U.S. Appl. No. 18/031,416, dated Jul. 1, 2026.

* cited by examiner

*Primary Examiner* — Lianko G Garyu
*Assistant Examiner* — David Paul Bowles
(74) *Attorney, Agent, or Firm* — Birch, Stewart, Kolasch & Birch, LLP

(57) ABSTRACT

The disclosures herein relate to novel compounds of formula (1) and salts thereof, wherein Q, X, $AA^1$, $AA^2$, $AA^3$, $AA^4$, $AA^5$, $AA^6$, $AA^7$, $AA^8$, $R^1$, $R^2$ and n are defined herein, and their use in treating, preventing, ameliorating, controlling or reducing the risk of disorders associated with apelin receptors.

(I)

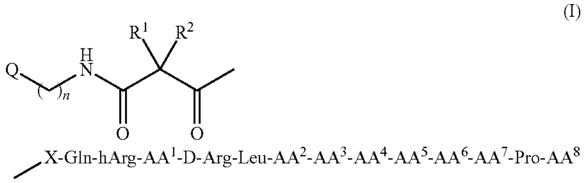

20 Claims, No Drawings

Specification includes a Sequence Listing.

CYCLIC APELIN RECEPTOR AGONISTS

This invention relates to a class of novel peptide compounds, their salts, pharmaceutical compositions containing them and their use in therapy of the human body. In particular, the invention is directed to a class of compounds which are agonists of Apelin receptors. The invention also relates to the manufacture and use of these compounds and compositions in the prevention or treatment of such diseases in which Apelin receptors are involved.

The compounds relates to metabolically stable apelin analogs, covering and range of G protein-dependent and independent pharmacological profiles, and their use under both acute and chronic administration protocols, for the prevention or the treatment of disease mediated by the apelin receptor, in particular of cardiovascular disease (heart failure, kidney failure, hypertension, pulmonary hypertension, acute and chronic kidney injury and thrombotic diseases), diabetes, liver and gastrointestinal disease.

REFERENCE TO SEQUENCE LISTING SUBMITTED VIA EFS-WEB

This application includes an electronically submitted sequence listing in .txt format. The .txt file contains a sequence listing entitled "2026-07-24_SequenceListing_3663-0132PUS1_ST25.txt" created on Jul. 24, 2026 and is 7,476 bytes in size. The sequence listing contained in this .txt file is part of the specification and is hereby incorporated by reference herein in its entirety.

BACKGROUND OF THE INVENTION

Apelin is the endogenous ligand of the apelin receptor (also known as APJ, APLNR or angiotensin receptor-like 1). The Apelin receptor is a class A GPCR located on chromosome 11 consisting of 377 amino acids. To date only one apelin receptor has been identified in mammals, although two subtypes are present in amphibians and fish, and there are no closely related (homologous) genes.

In humans the APLN gene resides on chromosome X and encodes a 77 amino acid precursor preproapelin which is subsequently proteolytically cleaved to generate several isoforms: apelin-36, apelin-17, apelin-13 and [Pyr1] apelin-13. Among the isoforms [Pyr1] apelin-13 is the predominant isoform detected in human heart and plasma, however the plasma half life of apelin is very short (<5 minutes) and therefore it is feasible additional short-lived isoforms with alternative structures and/or pharmacological properties may exist and potentially contribute to the physiological effects associated with the parent peptide apelin-36. Binding of the apelins to the apelin receptor can result in activation of multiple intracellular signaling pathways mediated by Gαi/o, Gα13 and possibly Gαq G proteins leading to recruitment of several signal transduction cascades including, but not limited to, phospholipase C (PLC), protein kinase C (PKC), AMP-activated protein kinase (AMPK), endothelial nitric oxide synthase, regulation of ERK1/2 phosphorylation and PI3K/Akt/p70S6 kinase signaling.

A second peptide of 54 amino acids Elabela/Toddler (ELABELA, or ELA, also known as Toddler, or Apela) has been identified which also activates the apelin receptor. The primary amino acid sequence of ELA does not demonstrate similarity to APJ however like APJ, ELA also undergoes rapid proteolytical cleavage to generate shorter isoforms. Both ligands are critical regulators of cardiovascular development and function.

Activation of the apelin receptor by endogenous ligands has also been demonstrated to result in the of β-arrestin, a protein that initiates receptor internalisation, desensitisation as well as downstream signalling. Recruitment of β-arrestin results in apparent short duration responses and an apelin receptor population that are refractory to further ligand-mediated activation. In various embodiments the identified examples can binding to and/or activate G protein-signalling either alone or in combination with recruitment of β-arrestin thereby providing unique pharmacological profiles useful in the treatment of diseases related to apelin dysfunction.

Both apelin and APJ are relatively widely expressed across the central nervous system (CNS), peripheral tissues and blood, suggesting roles in multiple complex physiological processes. Based on multiple literature publications the apelin system has been implicated in roles in CNS disorders, thermoregulation, glucose homeostasis, angiogenesis, diabetes, pancreatitis, cardiovascular function, hepatic function and renal function, cancer (including but not limited to glioblastoma and colon cancer), The APJ receptor and its ligands (apelin and ELA) have been implicated in the pathophysiology of human heart failure. Apelin receptors are present on endothelial cells, vascular smooth muscle cells and cardiomyocytes. Initial studies identified apelin as one of the most potent inotropic agents identified to date through direct actions on cardiomyocyte contractility without evidence of cardiac hypertrophy. Apelin has also been demonstrated to increase left ventricular contractility.

Apelin expression has been demonstrated to be altered in the setting of cardiovascular disease. An increase in apelin immunoreactivity has been observed in the plasma of patients in the early stages of heart failure, whereas a decrease is observed at later, more severe stages. Moreover, apelin receptor mRNA has been shown to be decreased in rat hypertrophied and failing hearts. Apelin gene-deficient mice were shown to develop an impaired heart contractility and progressive heart failure associated with aging and pressure overload. Therefore, down-regulation of the apelin system seems to coincide with declining cardiac performance raising the possibility that apelin could be a protective agent for cardiac function.

Systemic injection of apelin in rodents and humans has been demonstrated to result in significant decreases in blood pressure (BP) in rats via nitric oxide production. These data demonstrate that apelin exerts a hypotensive effect in vivo. However these effects on both blood pressure and inotropic cardiac output are short-lived, lasting only a few minutes, and demonstrating a degree of desensitization (also known as tachyphalaxis) leaving the apelin receptor refractory to further stimulation.

In chronic models of right ventricular failure apelin had inotropic effects and long-term treatment led to improved right ventricular mass, increased contractile force with decreased cardiac loading and hemodynamic measurements. Consistent with these findings apelin infusion has been demonstrated to improve pulmonary vascular hemodynamics in multiple preclinical models of pulmonary arterial hypertension (PAH) and these benefits have been confirmed to translate into PAH patients.

In zebrafish, ELA signalling is required for normal heart and vasculature development and its deficiency lead to severe defects in heart development and lymphogenesis. In humans ELA is expressed in adult embryonic stem cells and kidney and activates the human apelin receptor in respect of its activities to suppress cAMP production and to induce ERK1/2 phosphorylation and calcium mobilization. Functionally Elabela stimulates angiogenesis in human HUVECs and relaxes mouse aortic vessels.

In addition to a cardiovascular action of apelin, apelin receptor mRNA has been detected in all renal zones, most abundantly in the inner stripe of the outer medulla, in the glomeruli and a moderate expression was observed in all nephron segments, especially in collecting ducts. In agreement with this localization, the intravenous (iv) injection of apelin in increasing doses, dose-dependently increases diuresis.

Apelin expression has also been confirmed in human endothelial tissue where a key role in controlling fatty acid transport across the endothelial layer through apelin-induced inactivation of the transcription factor Forkhead box protein O1 (FOXO1) and subsequent inhibition of endothelial fatty acid binding protein 4 (FABP4) expression. These actions are consistent with predicted benefits on glucose utilisation and improved insulin sensitivity in diseases such as type 2 diabetes (T2DM).

Apelin receptor agonists may be useful alone and/or in combination with current standard of care treatments in the treatment of pulmonary arterial hypertension (PAH) increasing cardiac output, reducing pulmonary vessel hypertension, reducing inflammation, improve pulmonary-tissue remodelling and preserving right heart ventricular function. PAH is a rare, progressive disorder characterized by high blood pressure (hypertension) in the arteries of the lungs (pulmonary artery) for no apparent reason. Symptoms of PAH include shortness of breath (dyspnea) especially during exercise, chest pain, and fainting episodes. The exact cause of PAH is unknown and although treatable, there is no known cure for the disease. PAH occurs twice as frequently in females as in males. It tends to affect females between the ages of 30 and 60. New cases are estimated to occur in one to two individuals per million each year in the U.S. The incidence is estimated to be similar in Europe. Approximately 500-1000 new cases of PAH are diagnosed each year in the U.S. There is no ethnic or racial group that is known to have a higher frequency of patients with PAH. Individuals with PAH may go years without a diagnosis, either because their symptoms are mild, nonspecific, or only present during demanding exercise. However, it is important to treat PAH because without treatment high blood pressure in the lungs causes the right heart to work much harder, and over time, this heart muscle may weaken or fail. The progressive nature of this disease means that an individual may experience only mild symptoms at first, but will eventually require treatment and medical care to maintain a normal lifestyle.

Apelin receptor agonists are agents useful in the treatment of cardiovascular conditions such as heart failure, acute decompensated heart failure, congestive heart failure, cardiomyopathy, ischemia, ischemia/reperfusion injury, fluid homeostasis, kidney failure, hypertension, pulmonary hypertension, polycystic kidney disease, hyponatremia and SIADH to increase cardiac output, improve cardiac function, stabilise cardiac function, limit further decrease in cardiac function, reduce systemic and portal hypertension, promote angiogenesis and new blood vessel formation in ischemic tissue, treat abnormalities in thrombosis and platelet function and improve kidney function and diuresis. Heart failure constitutes a major and growing health burden. In Europe there are at least 15 million patients with heart failure and in the United States, heart failure affects nearly 5,800,000 people. Heart failure incidence approaches 10 per 1,000 population after age 65. In the United States, heart failure causes 280,000 deaths annually, and the estimated direct and indirect cost of heart failure for 2010 is $39.2 billion. Treatment options depend on the type, cause, symptoms and severity of the heart failure, including treating the underlying causes and lifestyle changes. A number of medications are prescribed or heart failure, and most patients will take more than one drug. Apelin receptor agonists are likely to be used on top of existing agents Despite the advancements obtained in medical therapy, the death rate of heart failure remains high: almost 50% of people diagnosed with heart failure will die within 5 years.

Abnormalities in platelet function are associated with a range of thrombotic diseases such as peripheral arterial disease (PAD), acute coronary syndrome (ACS), myocardial infarction (MI), heart attacks (HA), stroke and atherosclerosis. Apelin and APJNR are expressed in human and mouse platelets and apelin knockout mice displayed a prothrombotic phenotype with increased platelet aggregation. Stimulation of platelets with apelin has been demonstrated to engage signalling pathways associated with calcium, nitric oxide and thromboxane production consistent with predicted benefits in these conditions.

Apelin receptor agonists are also agents useful for the treatment and management of diabetes and associated related metabolic conditions, diabetic complications (for example diabetic nephropathy, retinopathy, neuropathy, non-alcoholic fatty liver disease, non-alcoholic steatosis, portal hypertension) and conditions where stimulation and/or growth and/or endurance of muscle mass may be considered beneficial. Apelin has been demonstrated to be expressed in endothelial cells and improved glucose tolerance, enhances glucose utilisation by muscle, increases muscle insulin sensitivity and improves angiogenesis in tissue with poor local blood supply. Apelin-neuroprotection, where administration of apelin peptides promote neuronal survival and/or increased numbers of neurons, will be useful in conditions with neuronal loss of function, such as diabetic neuropathy.

The half-life of apelin in the blood circulation is around one minute, this invention aims at designing, synthesising and testing novel potent and stable drugs that activate the apelin/apelin receptor pathway. Embodiments contained herein exemplify the potential to specifically activate intracellular signaling pathways in a manner independent of β-arrestin activation and consistent with sustained receptor activation in the absence of desensitisation and/or tachyphalaxis. Such a compound constitutes a potential new therapeutic agent to treat diseases mediated by the apelin receptor as described in this invention.

SUMMARY OF THE INVENTION

The present invention relates to novel compounds with agonist activity at the Apelin receptor, pharmaceutical compositions comprising these, and use of the compounds for the manufacture of medicaments for treatment of diseases.

Accordingly, in one embodiment the invention provides a compound of the formula (1):

(1)

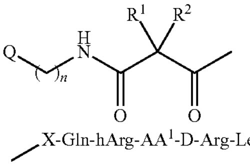

X-Gln-hArg-AA$^1$-D-Arg-Leu-AA$^2$-AA$^3$-AA$^4$-AA$^5$-AA$^6$-AA$^7$-Pro-AA$^8$ (SEQ ID NO:7)

wherein;

Q is selected from phenyl or a monocyclic heteroaryl ring each of which may be optionally substituted with one or more $R^q$ groups; or Q is a polyether chain of formula $—(OCH_2CH_2)_mOCH_3$, wherein m is 1 to 5;

$R^q$ is selected from halogen, hydroxyl, amino or $C_{1-6}$ alkyl having an alkyl chain optionally containing one or more heteroatoms selected from O, N, or S;

n is 1 to 3;

$R^1$ and $R^2$ are independently selected from hydrogen or a $C_{1-6}$ alkyl group, or together with the carbon to which they are attached join to form a $C_{3-8}$ cycloalkyl or a heterocyclyl group;

X is -DArg- or a bond;

-hArg- is a homoarginine residue;

$AA^1$ is the residue:

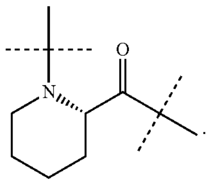

or is an aspartic acid derived residue joined to $AA^3$ via a lactam bridge;

$AA^2$ is -Gly- or is a glutamic acid derived residue joined to $AA^5$ via a lactam bridge;

$AA^3$ is -His-, a 4-bromophenylalanine residue or is a lysine derived residue joined to $AA^1$ via a lactam bridge;

$AA^4$ is the residue:

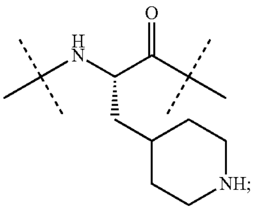

$AA^5$ is -Gly- or is a lysine derived residue joined to $AA^2$ via a lactam bridge;

$AA^6$ is the residue:

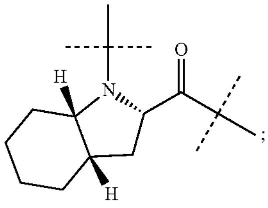

$AA^7$ is a norleucine residue or a 4-bromophenylalanine residue;

$AA^8$ is the residue:

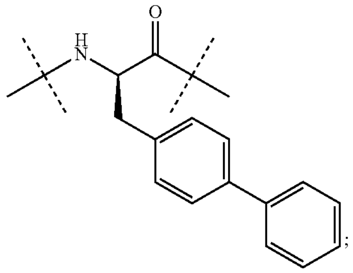

wherein the $AA^8$ C-terminus is a carboxyl group or a carboxamide group and wherein the compound contains a lactam bridge;

or a tautomeric or stereochemically isomeric form thereof or a prodrug, salt or zwitterion thereof.

DETAILED DESCRIPTION OF THE INVENTION

This invention relates to novel compounds. The invention also relates to the use of novel compounds as agonists of Apelin receptors. The invention further relates to the use of novel compounds in the manufacture of medicaments for use as Apelin receptor agonists or for the treatment of disorders associated with Apelin receptors.

The invention further relates to compounds, compositions and medicaments useful for the treatment of disorders associated with Apelin receptors. Such disorders include cardiovascular disease, acute decompensated heart failure, congestive heart failure, myocardial infarction, cardiomyopathy, ischemia, ischemia/reperfusion injury, pulmonary hypertension, diabetes, obesity, cancer, metastatic disease, fluid homeostasis, pathological angiogenesis, retinopathy, HIV infection, treatment of pulmonary arterial hypertension (PAH) increasing cardiac output, reducing pulmonary vessel hypertension, reducing inflammation, improve pulmonary tissue remodelling, preserving right heart ventricular function, heart failure, congestive heart failure, cardiomyopathy, ischemia, ischemia/reperfusion injury, fluid homeostasis, kidney failure, hypertension, pulmonary hypertension, polycystic kidney disease, hyponatremia, SIADH, platelet function are associated with a range of thrombotic diseases such as peripheral arterial disease (PAD), acute coronary syndrome (ACS), myocardial infarction (MI), heart attacks (HA), stroke, atherosclerosis, treatment and management of diabetes and associated related metabolic conditions, diabetic complications (for example diabetic nephropathy, retinopathy, neuropathy, non-alcoholic fatty liver disease, non-alcoholic steatosis, portal hypertension) and conditions where stimulation and/or growth and/or endurance of muscle mass may be considered beneficial.

Another aspect of the invention is a method of treating the symptoms of various forms of central nervous system disorders including, dementia, including senile dementia and cerebrovascular dementia, depression, hyperkinetic (minimal brain damage) syndrome, disturbance of consciousness, anxiety disorder, schizophrenia, phobia, epilepsy, amyotrophic lateral sclerosis; Impairments of growth hormone secretion and/or function including but not limited to hyperphagia, polyphagia, hypercholesterolemia, hyperglyceridemia, hyperlipidemia, hyperprolactinemia, hypoglycemia, hypopituitarism, pituitary dwarfism; cancers, pancreatitis, renal diseases, Turner's syndrome, rheumatoid arthritis, spinal injury, spinocerebellar deformation, bone fractures, wounds, atopic dermatitis, osteoporosis, asthma, infertility, arteriosclerosis, pulmonary emphysema, pulmonary edema, and milk secretion insufficiency, and can also be used as a hypnotic sedative, a postoperative nutritional status improving agent, a preventive or therapeutic drug for HIV infection, AIDS, etc., and the like, comprising administering a Apelin acting polypeptide to a patient in need thereof.

Diseases or conditions for which the compounds may be beneficial include those selected from the group consisting of, treatment of pulmonary arterial hypertension (PAH) increasing cardiac output, reducing pulmonary vessel hypertension, reducing inflammation, improve pulmonary tissue remodelling and preserving right heart ventricular function, heart failure, congestive heart failure, cardiomyopathy, ischemia, ischemia/reperfusion injury, fluid homeostasis, kidney failure, hypertension, pulmonary hypertension, polycystic kidney disease, hyponatremia and SIADH, treatment and management of diabetes and associated related metabolic conditions, diabetic complications (for example diabetic nephropathy, retinopathy, neuropathy, non-alcoholic fatty liver disease, non-alcoholic steatosis, portal hypertension) and conditions where stimulation and/or growth and/or endurance of muscle mass.

In a further aspect, the present invention provides the use of a compound as outlined above for the manufacture of a medicament for the treatment of any of the indications listed above.

Accordingly, in one embodiment the invention provides a compound of the formula (1):

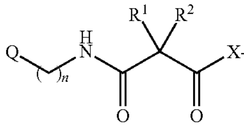X-Gln-hArg-$AA^1$-D-Arg-Leu-$AA^2$-$AA^3$-$AA^4$-$AA^5$-$AA^6$-$AA^7$-Pro-$AA^8$ wherein;

Q is selected from phenyl or a monocyclic heteroaryl ring each of which may be optionally substituted with one or more $R^q$ groups; or Q is a polyether chain of formula —$(OCH_2CH_2)_mOCH_3$, wherein m is 1 to 5;

$R^q$ is selected from halogen, hydroxyl, amino or $C_{1-6}$ alkyl having an alkyl chain optionally containing one or more heteroatoms selected from O, N, or S;

n is 1 to 3;

$R^1$ and $R^2$ are independently selected from hydrogen or a $C_{1-6}$ alkyl group, or together with the carbon to which they are attached join to form a $C_{3-8}$ cycloalkyl or a heterocyclyl group;

X is -DArg- or a bond;

-hArg- is a homoarginine residue;

$AA^1$ is the residue:

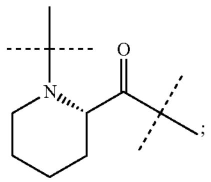

or is an aspartic acid derived residue joined to $AA^3$ via a lactam bridge;

$AA^2$ is -Gly- or is a glutamic acid derived residue joined to $AA^5$ via a lactam bridge;

$AA^3$ is -His-, a 4-bromophenylalanine residue or is a lysine derived residue joined to $AA^1$ via a lactam bridge;

$AA^4$ is the residue:

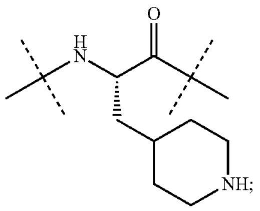

$AA^5$ is -Gly- or is a lysine derived residue joined to $AA^2$ via a lactam bridge;

$AA^6$ is the residue:

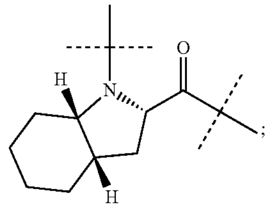

$AA^7$ is a norleucine residue or a 4-bromophenylalanine residue;

$AA^8$ is the residue:

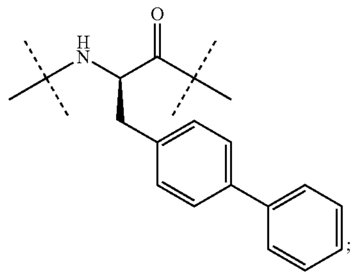

wherein the $AA^8$ C-terminus is a carboxyl group or a carboxamide group and wherein the compound contains a lactam bridge;

or a tautomeric or stereochemically isomeric form thereof or a prodrug, salt or zwitterion thereof.

Q can be selected from:

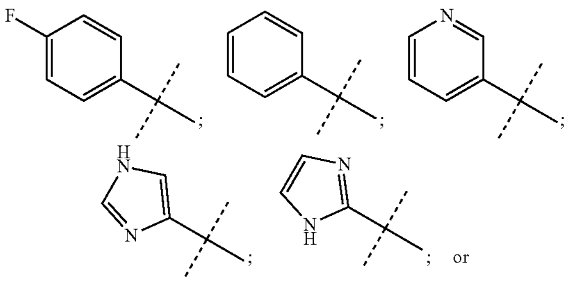

or

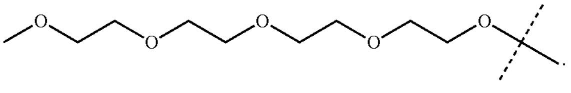

Q can be an imidazole ring. Q can be:

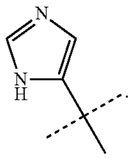

n can be 1. n can be 2. n can be 3.

$R^1$ and $R^2$ may be independently selected from hydrogen or a $C_{1-6}$ alkyl group. $R^1$ can be hydrogen or a $C_{1-6}$ alkyl group. $R^2$ can be hydrogen or a $C_{1-6}$ alkyl group. $R^1$ and $R^2$ can both be methyl. $R^1$ can be methyl. $R^2$ can be methyl.

X can be -DArg-. X can be a bond.

$AA^1$ can be the residue

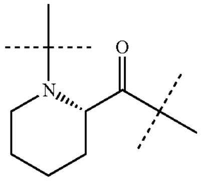

(homoproline). $AA^1$ can be an aspartic acid derived residue joined to $AA^3$ via a lactam bridge. Where the lactam bridge is between $AA^1$ and $AA^3$, $AA^2$ is -Gly- and $AA^5$ is -Gly.

$AA^2$ can be -Gly-. $AA^2$ can be a glutamic acid derived residue joined to $AA^5$ via a lactam bridge. Where the lactam bridge is between $AA^2$ and $AA^5$, $AA^1$ is -homoproline- and $AA^3$ is -His- or 4-bromophenylalanine.

$AA^3$ can be -His-. $AA^3$ can be a 4-bromophenylalanine residue. $AA^3$ can be a lysine derived residue joined to $AA^1$ via a lactam bridge. Where the lactam bridge is between $AA^1$ and $AA^3$, $AA^2$ is -Gly- and $AA^5$ is -Gly-.

$AA^5$ can be -Gly-. $AA^5$ can be a lysine derived residue joined to $AA^2$ via a lactam bridge. Where the lactam bridge is between $AA^2$ and $AA^5$, $AA^1$ is -homoproline- and $AA^3$ is -His- or 4-bromophenylalanine.

$AA^7$ can be norleucine. $AA^7$ can be 4-bromophenylalanine.

The $AA^8$ C-terminus can be a carboxyl group. The $AA^8$ C-terminus can be a carboxamide group.

All compounds described herein contain a single lactam bridge to internally cyclise the peptide sequence. The lactam bridge is between the side chain amino group of a lysine moiety at positions $AA^3$ or $AA^5$ and a side chain aspartic acid or glutamic acid. at positions $AA^1$ or $AA^2$. Specifically the lactam bridge can be between an aspartic acid at $AA^1$ and a lysine at $AA^3$. Alternatively the lactam bridge can be between a glutamic acid at $AA^2$ and a lysine at $AA^5$. Where the lactam bridge is between $AA^1$ and $AA^3$, $AA^2$ is -Gly- and $AA^5$ is -Gly-. Where the lactam bridge is between $AA^2$ and $AA^5$, $AA^1$ is -homoproline- and $AA^3$ is -His- or 4-bromophenylalanine.

Particular Examples of Moiety

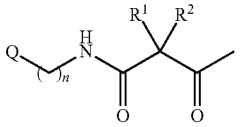

include caps 1-7 as shown below where the COOH group is coupled to the amine of the peptide X or $AA^1$ where X is a bond:

CAP 1

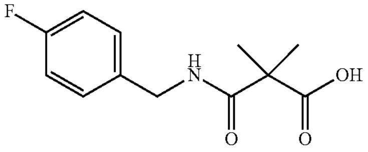

CAP 2

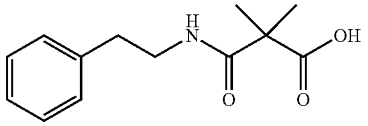

CAP 3

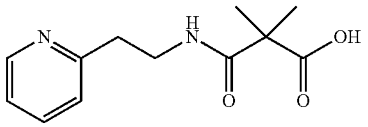

CAP 4

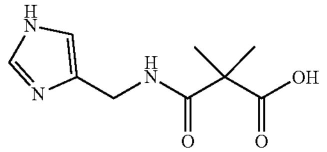

CAP 5

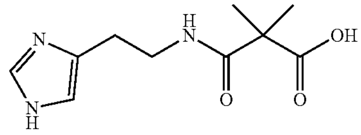

CAP 6

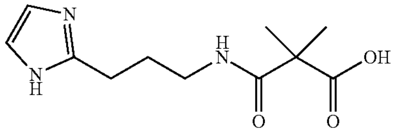

CAP 7

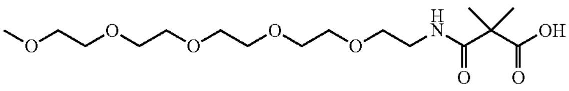

The compound can be selected from any one of Examples 1 to 6 as shown in Table 1.

Specific examples of compounds include compounds having Apelin receptor agonist activity.

The compounds of the invention may be used in a pharmaceutical composition comprising a compound of the invention and a pharmaceutically acceptable excipient.

The compounds of the invention may be used in medicine.

The compounds of the invention may be used in the treatment of disorders associated with Apelin receptors listed above.

Definitions

In this application, the following definitions apply, unless indicated otherwise.

The term "alkyl", "aryl", "halogen", "cycloalkyl", "heterocyclyl" and "heteroaryl" are used in their conventional sense (e.g. as defined in the IUPAC Gold Book) unless indicated otherwise.

The term "treatment", in relation to the uses of any of the compounds described herein, including those of the formula (1), is used to describe any form of intervention where a compound is administered to a subject suffering from, or at risk of suffering from, or potentially at risk of suffering from the disease or disorder in question. Thus, the term "treatment" covers both preventative (prophylactic) treatment and treatment where measurable or detectable symptoms of the disease or disorder are being displayed.

The term "effective therapeutic amount" as used herein (for example in relation to methods of treatment of a disorder, disease or condition) refers to an amount of the compound which is effective to produce a desired therapeutic effect. For example, if the condition is pain, then the effective therapeutic amount is an amount sufficient to provide a desired level of pain relief.

The desired level of pain relief may be, for example, complete removal of the pain or a reduction in the severity of the pain.

To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Salts or pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, potassium and calcium.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-sulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGA), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates. For a more detailed discussion of solvates and the methods used to make and characterise them, see Bryn et al, Solid-State Chemistry of Drugs, Second Edition, published by SSCI, Inc of West Lafayette, IN, USA, 1999, ISBN 0-967-06710-3.

The term "pharmaceutical composition" in the context of this invention means a composition comprising an active agent and comprising additionally one or more pharmaceutically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms.

The compositions may take the form, for example, of tablets, dragees, powders, elixirs, syrups, liquid preparations including suspensions, sprays, inhalants, tablets, lozenges, emulsions, solutions, cachets, granules, capsules and suppositories, as well as liquid preparations for injections, including liposome preparations.

The compounds of the invention may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$. In an analogous manner, a reference to a particular functional group also includes within its scope isotopic variations, unless the context indicates otherwise. For example, a reference to an alkyl group such as an ethyl group or an alkoxy group such as a methoxy group also covers variations in which one or more of the hydrogen atoms in the group is in the form of a deuterium or tritium isotope, e.g. as in an ethyl group in which all five hydrogen atoms are in the deuterium isotopic form (a perdeuteroethyl group) or a methoxy group in which all three hydrogen atoms are in the deuterium isotopic form (a trideuteromethoxy group). The isotopes may be radioactive or non-radioactive.

Therapeutic dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 10 μg to about 30 mg per kg body weight of a human and non-human animal, preferably from about 50 μg to about 30 mg per kg of body weight of a human and non-human animal, for example from about 50 μg to about 10 mg per kg of body weight of a human and non-human animal, for example from about 100 μg to about 30 mg per kg of body weight of a human and non-human animal, for example from about 100 μg to about 10 mg per kg of body weight of a human and non-human animal and most preferably from about 100 μg to about 1 mg per kg of body weight of a human and non-human animal.

Pharmaceutical Formulations

While it is possible for the active compound to be administered alone, it is preferable to present it as a pharmaceutical composition (e.g. formulation).

Accordingly, in another embodiment of the invention, there is provided a pharmaceutical composition comprising at least one compound of the formula (1) as defined above together with at least one pharmaceutically acceptable excipient.

The composition may be 6 composition suitable for injection. The injection may be intra-venous (IV) or subcutaneous. The composition may be supplied in a sterile buffer solution or as a solid which can be suspended or dissolved in sterile buffer for injection.

The pharmaceutically acceptable excipient(s) can be selected from, for example, carriers (e.g. a solid, liquid or semi-solid carrier), adjuvants, diluents (e.g solid diluents such as fillers or bulking agents; and liquid diluents such as solvents and co-solvents), granulating agents, binders, flow aids, coating agents, release-controlling agents (e.g. release retarding or delaying polymers or waxes); binding agents, disintegrants, buffering agents, lubricants, preservatives, anti-fungal and antibacterial agents, antioxidants, buffering agents, tonicity-adjusting agents, thickening agents, flavouring agents, sweeteners, pigments, plasticizers, taste masking agents, stabilisers or any other excipients conventionally used in pharmaceutical compositions.

The term "pharmaceutically acceptable" as used herein means compounds, materials, compositions, and/or dosage forms which are, within the scope of sound medical judgment, suitable for use in contact with the tissues of a subject (e.g. a human subject) without excessive toxicity, irritation, allergic response, or other problem or complication, commensurate with a reasonable benefit/risk ratio. Each excipient must also be "acceptable" in the sense of being compatible with the other ingredients of the formulation.

Pharmaceutical compositions containing compounds of the formula (1) can be formulated in accordance with known techniques, see for example, Remington's Pharmaceutical Sciences, Mack Publishing Company, Easton, PA, USA.

Suitable formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The compounds of the formula (1) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

The active compound will bi administered to a patient in need thereof (for example a human or animal patient) in an amount sufficient to achieve the desired therapeutic effect (effective amount). The precise amounts of compound administered may be determined by a supervising physician in accordance with standard procedures.

EXAMPLES

The invention will now be illustrated, but not limited, by reference to the specific embodiments described in the following examples.

Examples 1 to 6
Example 1
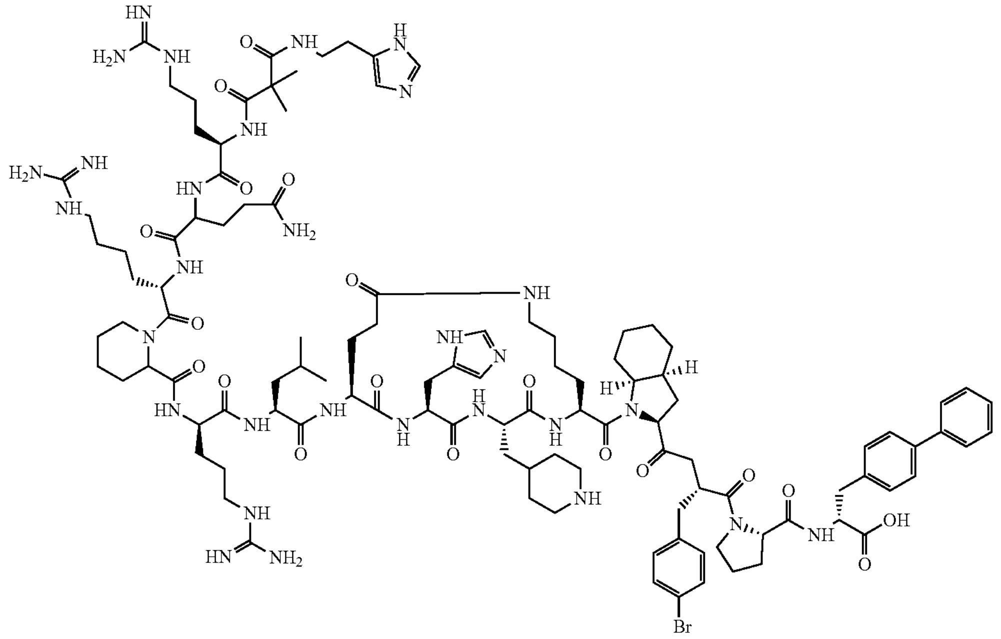
Example 2
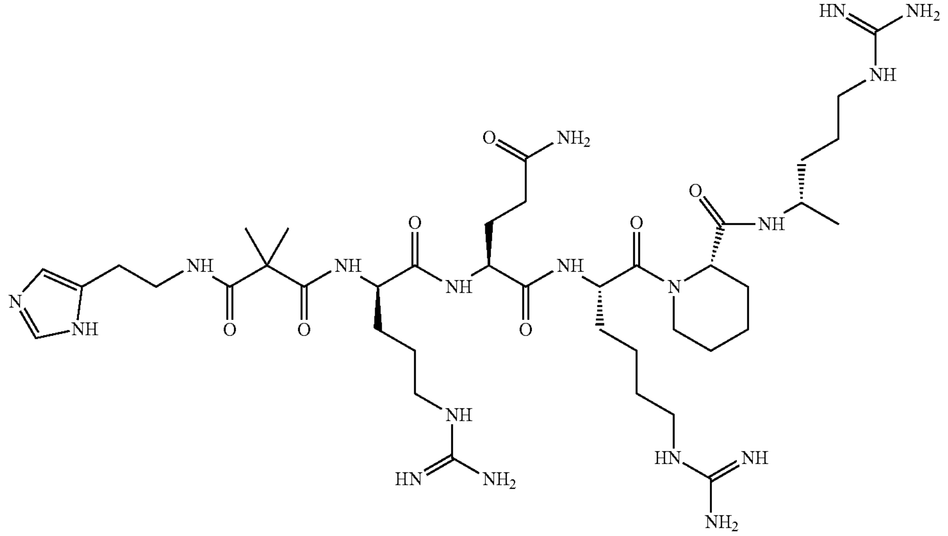
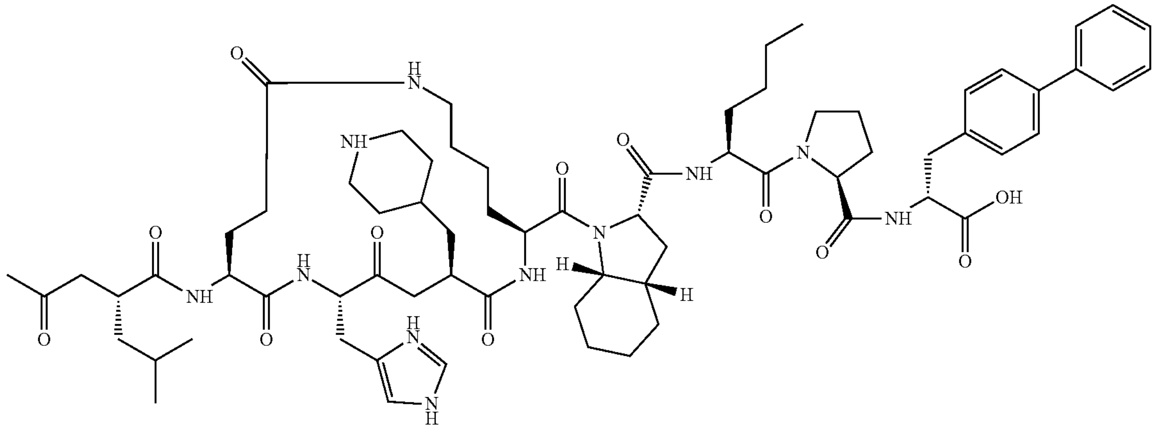

-continued
Example 3
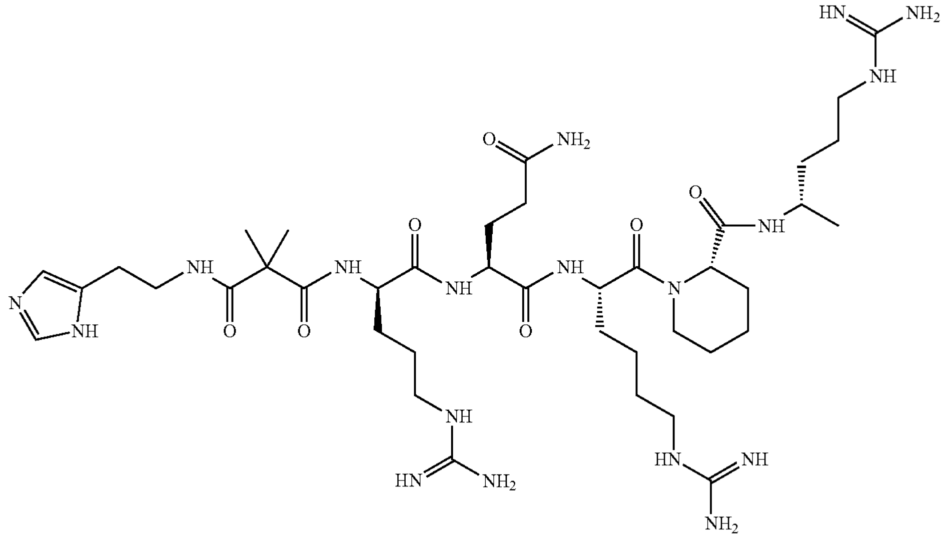
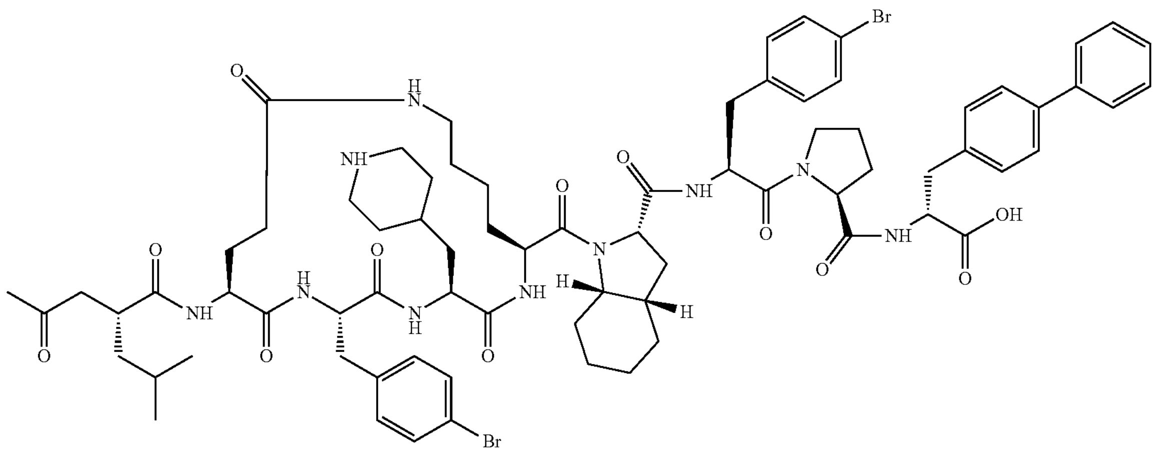
Example 4
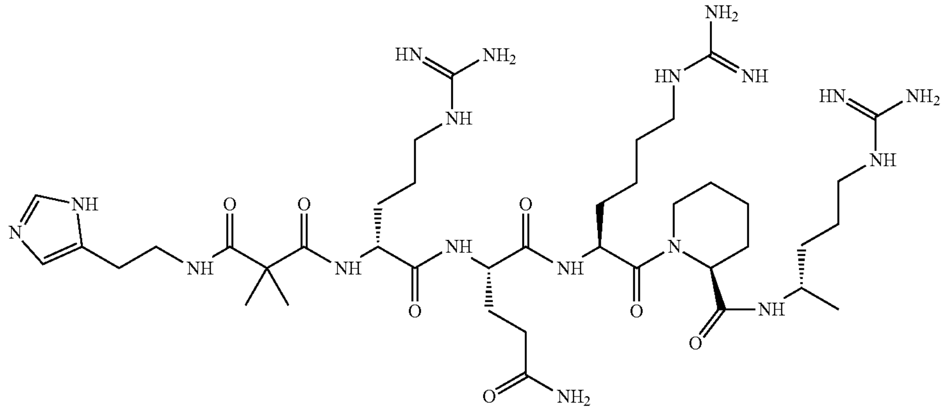

-continued
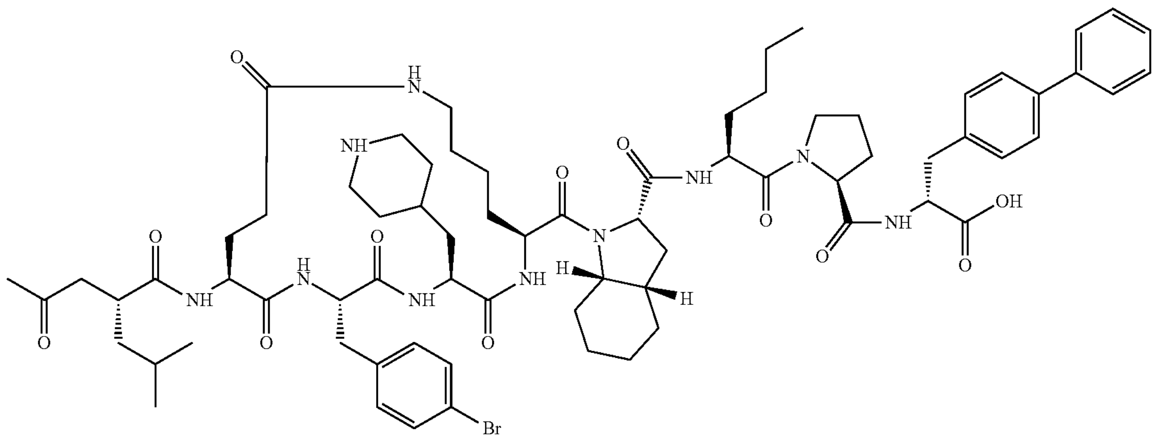
Example 5
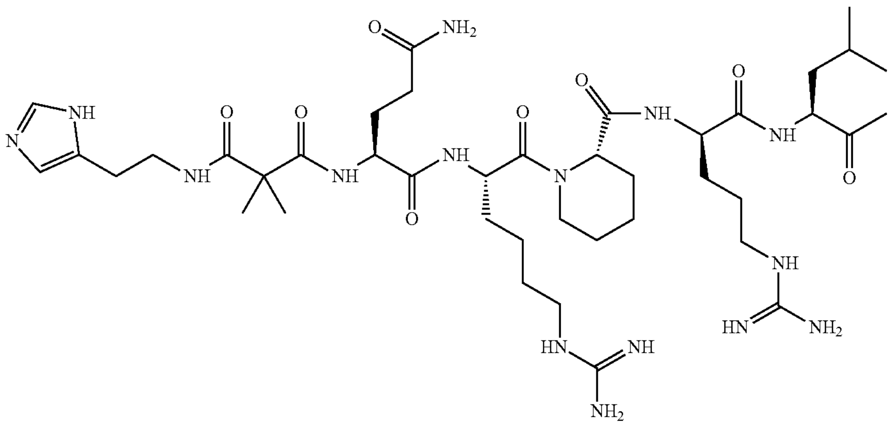
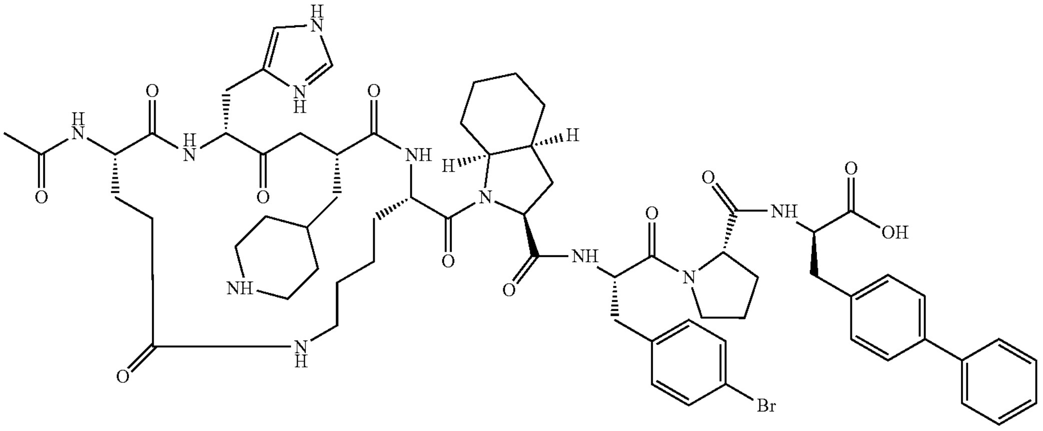

-continued

Example 6

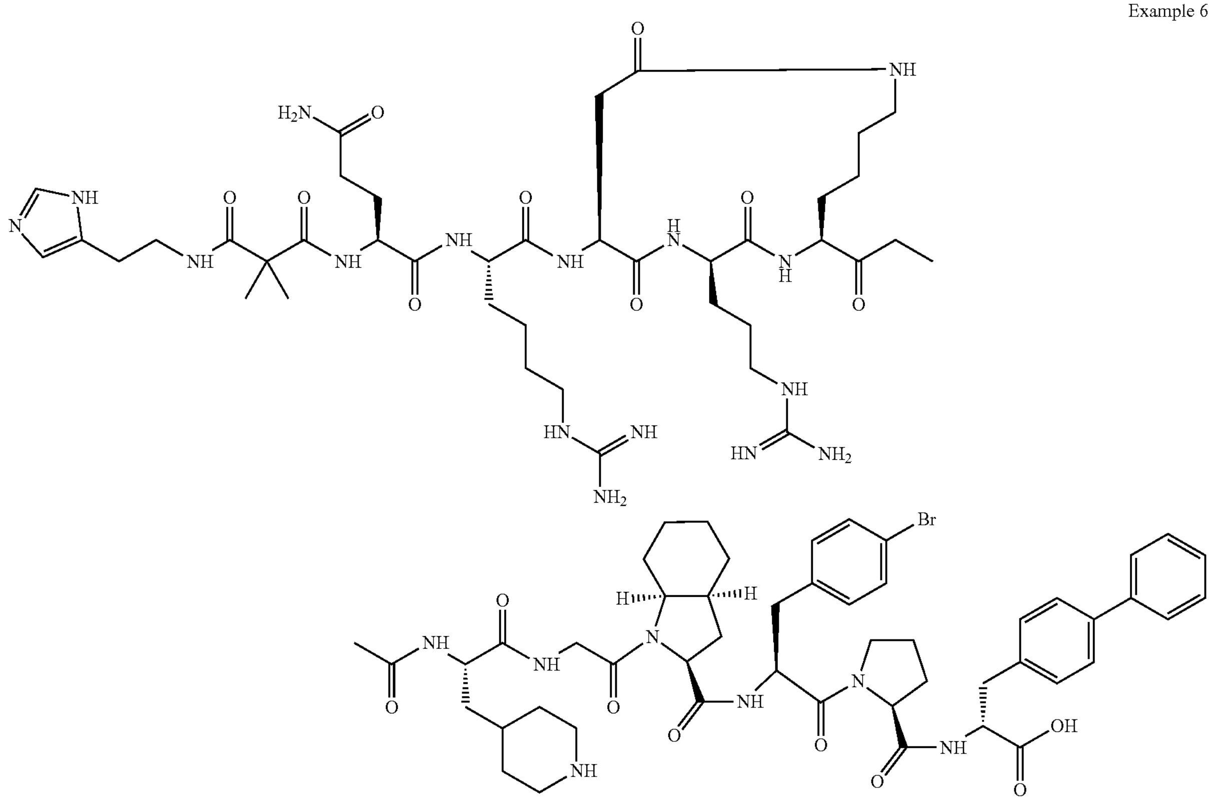

The compounds of Examples 1 to 6 shown in Table 1 below have been prepared. Their LCMS properties and the methods used to prepare them are set out in Table 2. The starting materials for each of the Examples are commercial unless indicated otherwise.

TABLE 1

| | 1 | 2 | 3 | 4 | 5 | 6 | 7 | 8 | 9 |
|---|---|---|---|---|---|---|---|---|---|
| Example 1 (SEQ ID NO:1) | CAP 5 | D-ARG | GLN | homoARG | homoPRO | D-ARG | LEU | CycloGLU | HIS |
| Example 2 (SEQ ID NO:2) | CAP 5 | D-ARG | GLN | HomoARG | HomoPRO | D-ARG | LEU | CycloGLU | HIS |
| Example 3 (SEQ ID NO:3) | CAP 5 | D-ARG | GLN | HomoARG | HomoPRO | D-ARG | LEU | CycloGLU | 4-BrPHE |
| Example 4 (SEQ ID NO:4) | CAP 5 | D-ARG | GLN | HomoARG | HomoPRO | D-ARG | LEU | CycloGLU | 4-BrPHE |
| Example 5 (SEQ ID NO:5) | | CAP 5 | GLN | HomoARG | HomoPRO | D-ARG | LEU | CycloGLU | HIS |
| Example 6 (SEQ ID NO:6) | | CAP 5 | GLN | HomoARG | CycloASP | D-ARG | LEU | GLY | CycloLYS |

| | 10 | 11 | 12 | 13 | 14 | 15 | 16 |
|---|---|---|---|---|---|---|---|
| Example 1 (SEQ ID NO:1) | PipALA | CycloLYS | OIC | 4-BrPHE | PRO | D-BIP | OH |
| Example 2 (SEQ ID NO:2) | PipALA | CycloLYS | OIC | NLE | PRO | D-BIP | OH |
| Example 3 (SEQ ID NO:3) | PipALA | CycloLYS | OIC | 4-BrPHE | PRO | D-BIP | OH |
| Example 4 (SEQ ID NO:4) | PipALA | CycloLYS | OIC | NLE | PRO | D-BIP | OH |
| Example 5 (SEQ ID NO:5) | PipALA | CycloLYS | OIC | 4-BrPHE | PRO | D-BIP | OH |
| Example 6 (SEQ ID NO:6) | PipALA | GLY | OIC | 4-BrPHE | PRO | D-BIP | OH |

Standard amino acid symbols are used in Table 1 where appropriate. In cases where a standard symbol is not available, the following representations are used:

CAP 1

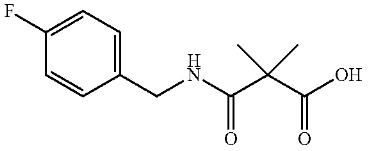

CAP 2

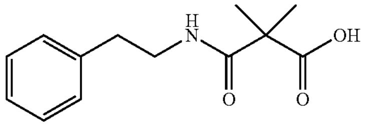

CAP 3

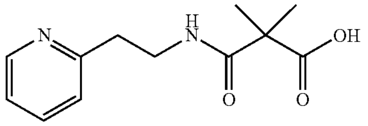

CAP 4

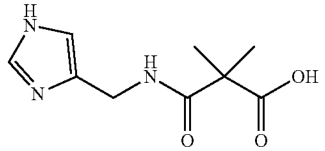

CAP 5

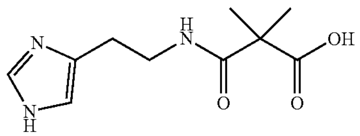

CAP 6

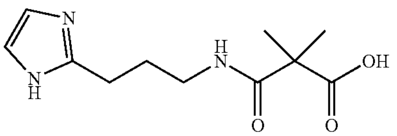

CAP 7

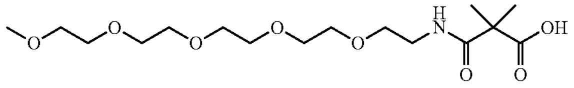

Standard amino acid symbols are used in Table 1 where appropriate. In cases where a standard symbol is not available, the following representations are used:

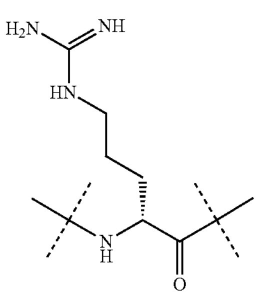

D-ARG

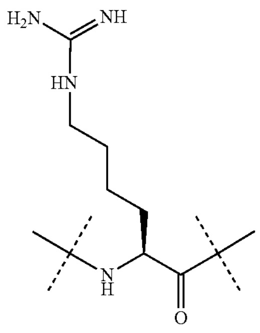

homoARG

-continued

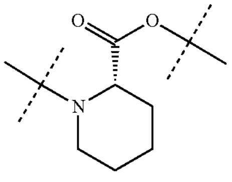

homoPRO

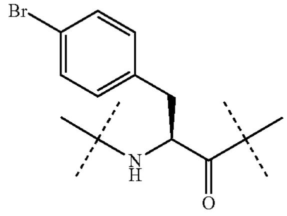

4-BrPHE

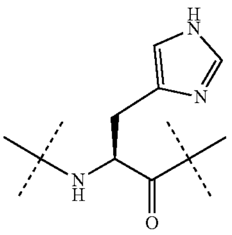

HIS

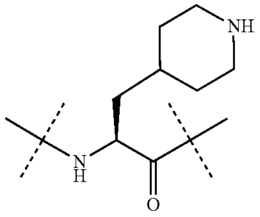

PipALA

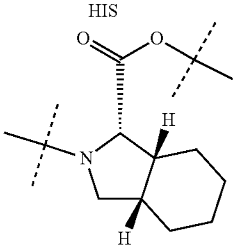

OIC

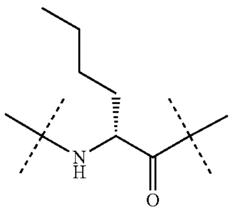

NorLEU/NLE

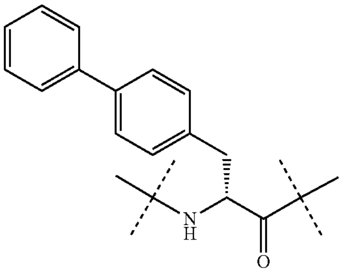

D-BIP

General Procedures

Where no preparative routes are included, the relevant intermediate is commercially available. Commercial reagents were utilized without further purification. Room temperature (rt) refers to approximately 20-27° C. $^{1}$H NMR spectra were recorded at 400 MHz on a Bruker instrument. Chemical shift values are expressed in parts per million (ppm), i.e. (δ)-values. The following abbreviations are used for the multiplicity of the NMR signals: s=singlet, br=broad, d=doublet, t=triplet, q=quartet, quint=quintet, td=triplet of doublets, tt=triplet of triplets, qd=quartet of doublets, ddd=doublet of doublet of doublets, ddt=doublet of doublet of triplets, m=multiplet. Coupling constants are listed as J values, measured in Hz. NMR and mass spectroscopy results were corrected to account for background peaks. Chromatography refers to column chromatography performed using 60-120 mesh silica gel and executed under nitrogen pressure (flash chromatography) conditions.

Analytical Methods

LCMS analysis of compounds was performed under electrospray conditions

LCMS Method A

Instruments: Waters Acquity UPLC, Waters 3100 PDA Detector, SQD; Column: Acquity HSS-T3, 1.8 micron, 2.1×100 mm; Gradient [time (min)/solvent B in A (%)]: 0.00/10, 1.00/10, 2.00/15, 4.50/55, 6.00/90, 8.00/90, 9.00/10, 10.00/10; Solvents: solvent A=0.1% trifluoroacetic acid in water; solvent B=acetonitrile; Injection volume 1 μL; Detection wavelength 214 nm; Column temperature 30° C.; Flow rate 0.3 mL per min.

Analytical Method B

MS ion determined using LCMS method below under electrospray conditions, HPLC retention time ($R_T$) determined using HPLC method below, purity>95% by HPLC unless indicated.

LCMS: Agilent 1200 HPLC&6410B Triple Quad, Column: Xbridge C18 3.5 μm 2.1*30 mm. Gradient [time (min)/solvent B (%)]:0.0/10, 0.9/80, 1.5/90, 8.5/5, 1.51/10. (Solvent A=1 mL of TFA in 1000 mL Water; Solvent B=1 mL of TFA in 1000 mL of MeCN); Injection volume 5 μL (may vary); UV detection 220 nm 254 nm 210 nm; Column temperature 25° C.; 1.0 mL/min.

HPLC: Agilent Technologies 1200, Column: Sepax GP-C18 5 μm 120 A 4.6*150 mm. Gradient [time (min)/solvent B (%)]:0.0/40, 20/55, 20.1/90, 23/90. (Solvent A=1 mL of TFA in 1000 mL Water; Solvent B=1 mL of TFA in 1000 mL of 80% MeCN+20% H2O); Injection volume 30 μL (may vary); UV detection 220 nm; Column temperature 25° C.; 1.0 mL/min Analytical Method C MS ion determined using LCMS method below under electrospray conditions, HPLC retention time ($R_T$) determined using HPLC method below, purity>95% by HPLC unless indicated.

LCMS: Agilent 1200 HPLC&6410B Triple Quad, Column: Xbridge C18 3.5 um 2.1*30 mm. Gradient [time (min)/solvent B (%)]:0.0/10, 0.9/80, 1.5/90, 8.5/5, 1.51/10. (Solvent A=1 mL of TFA in 1000 mL Water; Solvent B=1 mL of TFA in 1000 mL of MeCN); Injection volume 5 μL (may vary); UV detection 220 nm 254 nm 210 nm; Column temperature 25° C.; 1.0 mL/min.

HPLC: Agilent Technologies 1200, Column: Gemini-NX C18 5 um 110 A 150*4.6 mm. Gradient [time (min)/solvent B (%)]:0.0/30, 20/60, 20.1/90, 23/90. (Solvent A=1 mL of TFA in 1000 mL Water; Solvent B=1 mL of TFA in 1000 mL of MeCN); Injection volume 5 μL (may vary); UV detection 220 nm 254 nm; Column temperature 25° C.; 1.0 mL/min Analytical Method D Instrument: Thermo Scientific Orbitrap Fusion; Column: Phenomenex Kinetex Biphenyl 100 Å, 2.6 μm, 2.1×50 mm; Gradient [time (min)/solvent B in A (%)]: 0.00/10, 0.30/10, 0.40/60, 1.10/90, 1.70/90, 1.75/10, 1.99/10, 2.00/10; Solvents: Solvent A=0.1% formic acid in water; Solvent B=0.1% formic acid in acetonitrile; Injection volume 5 μL; Column temperature 25° C.; Flow rate 0.8 mL/min.

Synthesis of Intermediates and Compounds

The following examples are provided to illustrate preferred aspects of the invention and are not intended to limit the scope of the invention.

Synthesis of Intermediates

All Fmoc-amino acids are commercially available except for the Intermediate 1 building block, the synthesis of which is outlined below Synthesis of 2,2-dimethyl-3-oxo-3-((2-(1-trityl-1H-imidazol-4-yl)ethyl)amino)propanoic acid (Intermediate 1)

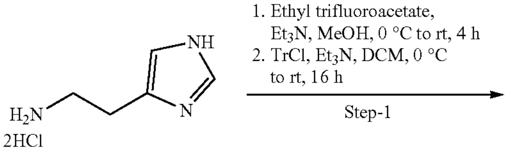

1

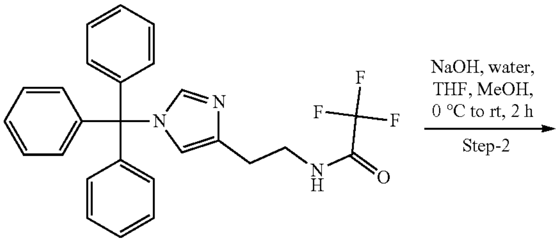

2

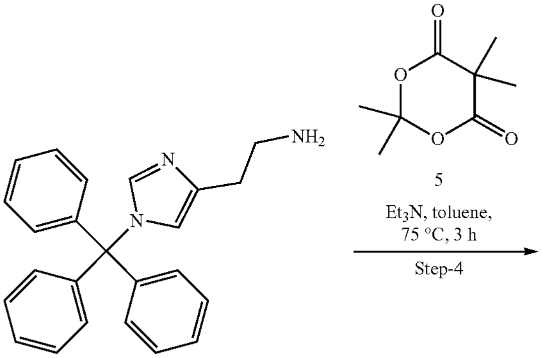

3

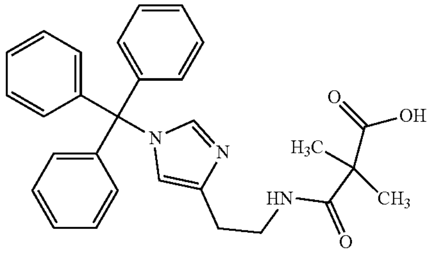

Intermediate 1

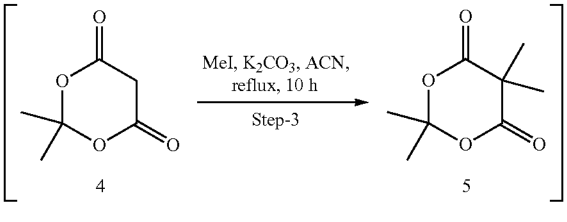

Step-1: Synthesis of 2,2,2-trifluoro-N-(2-(1-trityl-1H-imidazol-4-yl)ethyl)acetamide (2): To a solution of 2-(1H-imidazol-4-yl)ethan-1-amine dihydrochloride (1, 25.0 g, 136.6 mmol) in MeOH (100 mL), $Et_3N$ (67 mL, 464.4 mmol) was added at rt and the reaction mixture was cooled to 0° C. A solution of ethyl trifluoroacetate (20 mL, 164.0 mmol) in MeOH (50 mL) was added to the reaction mixture over 30 min at 0° C. and the reaction mixture was stirred at rt for 4 h. This reaction mixture was diluted with dry DCM (200 mL) and $Et_3N$ (60 mL, 409.8 mmol) and the reaction mixture was cooled to 0° C. Tr-Cl (76 g, 273.2 mmol) was added portion wise and the resulting reaction mixture was stirred a rt for 16 h. After completion, the reaction mixture was quenched with water (300 mL) and the aq layer was extracted with chloroform (3×150 mL). The organic layers were combined, dried ($Na_2SO_4$) and concentrated in vacuo. The crude residue was triturated with n-hexane to give 2,2,2-trifluoro-N-(2-(1-trityl-1H-imidazol-4-yl)ethyl)acetamide (2, 50.10 g, 81%) as a white solid.

MS (ESI+ve): 450

$^1$H-NMR (400 MHz; $CDCl_3$): δ 2.75 (t, J=5.9 Hz, 2H), 3.60-3.65 (m, 2H), 6.61 (s, 1H), 7.08-7.15 (m, 6H), 7.31-7.38 (m; 9H), 7.40 (s, 1H), 8.41 (bs, 1H).

Step-2: Synthesis of 2-(1-trityl-1H-imidazol-4-yl)ethan-1-amine (3): To a solution of 2,2,2-trifluoro-N-(2-(1-trityl-1H-imidazol-4-yl)ethyl)acetamide (2, 50.0 g, 111.3 mmol) in THE (150 mL) and MeOH (180 mL), NaOH (22.0 g, 556.7 mmol) in water (100 mL) was slowly added at 0° C. and the reaction mixture was stirred at room temperature for 2 h. After completion, the reaction mixture was quenched with water (300 mL) and the aq layer was extracted with chloroform (3×150 mL). The organic layers were combined, dried ($Na_2SO_4$) and concentrated in vacuo to give 2-(1-trityl-1H-imidazol-4-yl)ethan-1-amine (3, 34.0 g, 86%) as a yellowish sticky solid. The crude residue was used for the next step without further purification.

MS (ESI+ve): 354

$^1$H-NMR (400 MHz; $CDCl_3$): δ 1.53 (bs, 2H), 2.65 (t, J=6.5 Hz, 2H), 2.95 (t, J=6.5 Hz, 2H), 6.58 (s, 1H), 7.11-7.16 (m, 6H), 7.28-7.38 (m, 10H).

Step-3: Synthesis of 2,2,5,5-tetramethyl-1,3-dioxane-4,6-dione (5): To a solution of 2,2-dimethyl-1,3-dioxane-4,6-dione (4, 20.0 g, 138.8 mmol) in ACN (200 mL), $K_2CO_3$ (96 g, 694.0 mmol) and Mel (26 mL, 416.6 mmol) were added at rt and reaction mixture was refluxed for 10 h. After completion, the reaction mixture was cooled to room temperature, filtered through a pad of celite, washed with EtOAc (3×50 mL). The organic layer was washed with 10% aq $Na_2S2O_3$ (100 mL), dried, ($Na_2SO_4$) and concentrated in vacuo to give 2,2,5,5-tetramethyl-1,3-dioxane-4,6-dione (5, 21 g, 88%) as a yellow solid. The crude residue was used for the next step without further purification.

$^1$H-NMR (400 MHz; $CDCl_3$): δ 1.63 (s, 6H), 1.73 (s, 6H).

Step-4: Synthesis of 2,2-dimethyl-3-oxo-3-((2-(1-trityl-1H-imidazol-4-yl)ethyl)amino) propanoic acid (Intermediate 1): A solution of 2-(1-trityl-1H-imidazol-4-yl)ethan-1-amineto (3, 8.0 g, 22.6 mmol) and $Et_3N$ (16.0 mL, 113.0 mmol) in toluene (100 mL) was added drop wise over 60 min to a solution of 2,2,5,5-tetramethyl-1,3-dioxane-4,6-dione (5, 5.8 g, 29.76 mmol) in toluene (50 mL) at 75° C. The reaction mixture was further stirred at same temperature was 3 h. After completion, the reaction mixture was concentrated in vacuo. The residue was dissolved in chloroform (100 mL) and washed with 10% aq citric acid (pH~6-6.5). The organic layer was dried ($Na_2SO_4$) and concentrated in vacuo. The crude residue obtained was triturated with hot chloroform (150 mL) and n-hexane (75 mL) and the suspension was stirred at rt for 16 h. The solid was filtered, washed with chloroform:n-hexane (1:1, 2×50 mL) and dried in vacuo to give 2,2-dimethyl-3-oxo-3-((2-(1-trityl-1H-imidazol-4-yl)ethyl)amino)propanoic acid (Intermediate 1, 6.8 g, 64%) as a white solid.

LCMS (Method A): m/z 468 $[M+H]^+$ ($ES^+$), at 5.38 min, 99.31%

$^1$H-NMR (400 MHz; DMSO-$d_6$): δ 1.21 (s, 6H), 2.57 (t, J=6.8 Hz, 2H), 3.22-3.27 (m, 2H), 6.66 (s, 1H), 7.06-7.11 (m, 6H), 7.28 (s, 1H), 7.35-7.42 (m, 8H), 7.64 (t, J=5.4 Hz, 1H), 8.31 (s, 1H), 12.44 (bs, 1H).

Synthesis of Examples 1-6

Standard Fmoc solid phase peptide synthesis (SPPS) was used to synthesize the linear peptides which were then cleaved from the resin and purified.

General method for Peptide Synthesis: The peptide was synthesized using standard Fmoc chemistry.

Method a—Exemplified by the Synthesis of Example 2

Peptide Synthesis

1) Add DCM to the vessel containing CTC Resin (0.2 mmol) and Fmoc-D-Bip-OH (92.4 mg, 0.2 mmol, 1.0 eq) agitate with $N_2$ bubbling.
2) Drain and then wash with DMF (5 times, drain between each wash).
3) A solution of 20% piperidine in DMF was added agitate with $N_2$ bubbling for 30 min. 4) Drain and wash with DMF (5 times, drain between each wash).
5) Add Fmoc-amino acid solution (3.0 equivalents in DMF) and mix for 30 seconds, then add activation buffer (HBTU (2.85 equivalents) and DIEA (6 equivalents) in DMF), agitate with $N_2$ bubbling for 1 hour.
6) The coupling reaction was monitored by ninhydrin test
7) If required repeat steps 4 to 6 for same amino acid coupling if inefficient coupling occurs
8) Repeat steps 2 to 6 for next amino acid coupling.

Note: for the acids in the table below different protecting groups and/or coupling agents were used

| Step | Materials | Coupling reagents |
|---|---|---|
| 5 | Fmoc-Lys(Alloc)-OH (3.0 eq) | HBTU (2.85 eq) and DIEA (6.0 eq) |
| 8 | Fmoc-Glu(OAll)-OH (3.0 eq) | HBTU (2.85 eq) and DIEA (6.0 eq) |
| 15 | Intermediate 1 (2.0 eq) | HOAt (2.0 eq) and DIC (2.0 eq) |

Peptide Sidechain Deprotection Cyclisation:

1) Add DCM to the resin and agitate with $N_2$ bubbling, then add $PhSiH_3$ (10 eq), $Pd(PPh_3)_4$ (0.2 eq) agitate with $N_2$ for 15 mins for 3 times.
2) The resin was washed with DCM three times and then DMF three times.
3) The resin was washed with 0.5% Sodium diethyldithiocarbamate trihydrate DMF and 0.5% DIEA in DMF for ten times.
4) HATU (2 eq) and DIEA (4 eq) were added to the resin in DMF and agitate with $N_2$ bubbling for 1 hour.
5) The resin was washed with MeOH three times and dried in vacuo.

Peptide Cleavage and Purification:

1) Add cleavage buffer (92.5% TFA/2.5% EDT/2.5% TIS/2.5% $H_2O$) to the flask containing the side chain protected peptide on resin at room temperature and stir for 3 hours.
2) Filter and collect the peptide solution.
3) The peptide is precipitated with cold tert-butyl methyl ether and centrifuged (3 min at 3000 rpm).
4) Residue washed with tert-butyl methyl ether (2 times).
5) Crude peptide dried under-vacuum for 2 hours.
6) The crude peptide was purified by prep-HPLC. Prep-HPLC Conditions: Instrument: Gilson 281. Solvent: A—0.1% TFA in H2O, B—acetonitrile, Column: Luna C18 (200×25 mm; 10 μm) and Gemini C18 (150*30 mm; 5 μm) in series. Gradient [time (min)/solvent B (%)]:0.0/60, 60.0/90, 60.1/90, 70/90, 70.1/10, at 20 mL/min with UV detection (wave length=215/254 nm) and then lyophilized to give Example 2 (28.8 mg, 6.62% yield).

TABLE 2

| HRMS and LCMS properties of purify peptides represented by Examples 1-23 | | | |
|---|---|---|---|
| Example | HRMS (Method D) | Analytical Method | LCMS/HPLC |
| 1 | HRMS (HESI/FT) m/z: $[M + 4H]^{4+}$ Calcd for C109H160O19N31Br 2286.169; Found 572.5543 | B | m/z 1145.0 $[M + 2H]^{2+}$, $R_T$ = 11.31 min |
| 2 | HRMS (HESI/FT) m/z: $[M + 4H]^{4+}$ Calcd for C106H163O19N31 2174.2742; Found 544.5818 | C | m/z 726.1 $[M + 3H]^{3+}$, $R_T$ = 7.26 min |
| 3 | HRMS (HESI/FT) m/z: $[M + 4H]^{4+}$ Calcd for C112H161O19N29Br 2374.0891; Found 594.5337 | C | m/z 793.2 $[M + 3H]^{3+}$, $R_T$ = 11.57 min |
| 4 | HRMS (HESI/FT) m/z: $[M + 4H]^{4+}$ Calcd for C109H164O19N29Br 2262.1941; Found 566.5570 | C | m/z 755.7 $[M + 3H]^{3+}$, $R_T$ = 9.89 min |
| 5 | HRMS (HESI/FT) m/z: $[M + 4H]^{4+}$ Calcd for C103H148O18N27Br 2130.0679; Found 533.5250 | C | m/z 711.8 $[M + 3H]^{3+}$, $R_T$ = 9.83 min |
| 6 | HRMS (HESI/FT) m/z: $[M + 4H]^{4+}$ Calcd for C94H136O18N25Br 1981.9679; Found 496.4998 | C | m/z 662.2 $[M + 3H]^{3+}$ $R_T$ = 7.43 min |

ND—Not determined

Biological Activity

The following examples are provided to illustrate preferred aspects of the invention and are not intended to limit the scope of the invention.

Example A. In Vitro Pharmacological Characterization of Apelin Peptides—Functional Agonism of Human Apelin Receptors, cAMP Accumulation Assay cAMP functional assay. cAMP production was quantified using the Homogeneous Time-Resolved Fluorescence (HTRF) cAMP dynamic-2 assay (Cisbio, France). CHO cells stably expressing the human Apelin receptor were seeded at a density of 12,500 cells/well in solid walled 96 well half area plates (Costar). After 16 h incubation at 37° C. media was removed and cells were incubated at 37° C. for 30 min in serum free media containing 500 μM IBMX (Tocris), 3 uM forskolin to raise cAMP levels and increasing concentrations of test agonist. cAMP production was determined as manufacturer's instructions before plates were read on a PheraStar fluorescence plate reader (BMG LabTech) and $EC_{50}$ values were determined using Graphpad Prism™ (graphing and analysis software).

| | Human Apelin agonist cAMP assay | |
|---|---|---|
| Example | $pEC_{50}$ | Emax |
| Apelin | 8.9 | 112.8 |
| 1 | 8.5 | 70.5 |
| 2 | 7.8 | 31.2 |
| 3 | 8.1 | 27.9 |
| 4 | 7.0 | 28.4 |

-continued

| | Human Apelin agonist cAMP assay | |
|---|---|---|
| Example | $pEC_{50}$ | Emax |
| 5 | 8.3 | 48.2 |
| 6 | 7.9 | 30.5 |

Example B. In Vitro Pharmacological Characterization of Apelin Peptides—Functional Agonism of Human Apelin Receptors, β-Arrestin Accumulation Assay β-arrestin assay. CHO-K1 cells engineered to overexpress the human Apelin receptor and 3-arrestin (DiscoverRx) were seeded at a density of 12,500 cells/well in solid walled 96 well half area plates (Costar). After 16 h incubation at 37° C. media was removed and cells were incubated at 37° C. for 90 min in serum free media containing increasing concentrations of test agonist. The assay reaction was stopped by adding detection reagent (DiscoveRx) and incubation for 60 min in the dark. Levels of receptor activation were then measured on a PheraStar fluorescence plate reader (BMG LabTech) and $EC_{50}$ values were determined using Graphpad Prism™. Emax value only reported for active compounds.

| Example | Human Apelin agonist β-arrestin assay $pEC_{50}$ (Emax) |
|---|---|
| Apelin | 8.6 (165.8) |
| 1 | <5 |
| 2 | <5 |
| 3 | <5 |
| 4 | <5 |
| 5 | <5 |
| 6 | <4 |

The invention claimed is:

1. A compound comprising the sequence of formula (1):

(SEQ ID NO: 7)

(1)

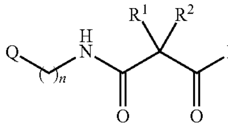 X-Gln-hArg-$AA^1$-D-Arg-Leu-

-$AA^2$-$AA^3$-$AA^4$-$AA^5$-$AA^6$-$AA^7$-Pro-$AA^8$ wherein;

Q is selected from phenyl or a monocyclic heteroaryl ring each of which may be optionally substituted with one or more $R^q$ groups; or Q is a polyether chain of formula —$(OCH_2CH_2)_mOCH_3$, wherein m is 1 to 5;

$R^q$ is selected from halogen, hydroxyl, amino or $C_{1-6}$ alkyl having an alkyl chain optionally containing one or more heteroatoms selected from O, N, or S;

n is 1 to 3;

$R^1$ and $R^2$ are independently selected from hydrogen or a $C_{1-6}$ alkyl group, or together with the carbon to which they are attached join to form a $C_{3-8}$ cycloalkyl or a heterocyclyl group;

X is -DArg- or a bond;

-hArg- is a homoarginine residue;

$AA^1$ is the residue:

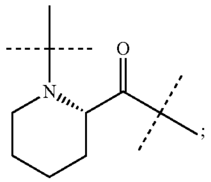

or is an aspartic acid derived residue joined to $AA^3$ via a lactam bridge;

$AA^2$ is -Gly- or is a glutamic acid derived residue joined to $AA^5$ via a lactam bridge;

$AA^3$ is -His-, a 4-bromophenylalanine residue or is a lysine derived residue joined to $AA^1$ via a lactam bridge;

$AA^4$ is the residue:

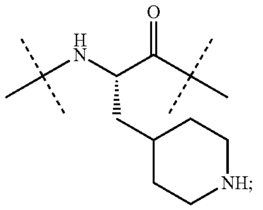

$AA^5$ is -Gly- or is a lysine derived residue joined to $AA^2$ via a lactam bridge;

$AA^6$ is the residue:

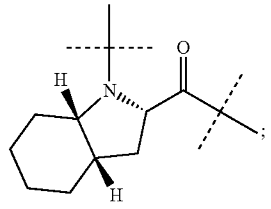

$AA^7$ is a norleucine residue or a 4-bromophenylalanine residue;

$AA^8$ is the residue:

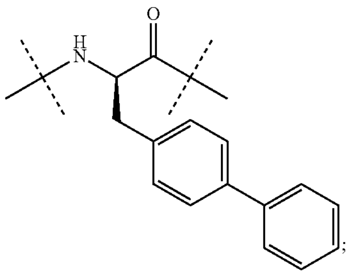

wherein the $AA^8$ C-terminus is a carboxyl group or a carboxamide group and wherein the compound contains a lactam bridge;

or a tautomeric or stereochemically isomeric form thereof or a prodrug, salt or zwitterion thereof.

2. The compound according to claim 1, wherein Q is:

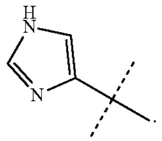

3. The compound according to claim 1, wherein n is 2.

4. The compound according to claim 1, wherein $R^1$ and $R^2$ are independently selected from hydrogen or a $C_{1-6}$ alkyl group.

5. The compound according to claim 4, wherein $R^1$ and $R^2$ are both methyl.

6. The compound according to claim 1, wherein X is -DArg-.

7. The compound according to claim 1, wherein X is a bond.

8. The compound according to claim 1, wherein $AA^1$ is an aspartic acid derived residue joined via a lactam bridge to $AA^3$ which is a lysine derived residue.

9. The compound according to claim 1, wherein $AA^2$ a glutamic acid derived residue joined via a lactam bridge to $AA^5$ which is a lysine derived residue.

10. The compound according to claim 1, wherein the $AA^8$ C-terminus is a carboxyl group.

11. The compound according to claim 1 which is selected from the group consisting of:

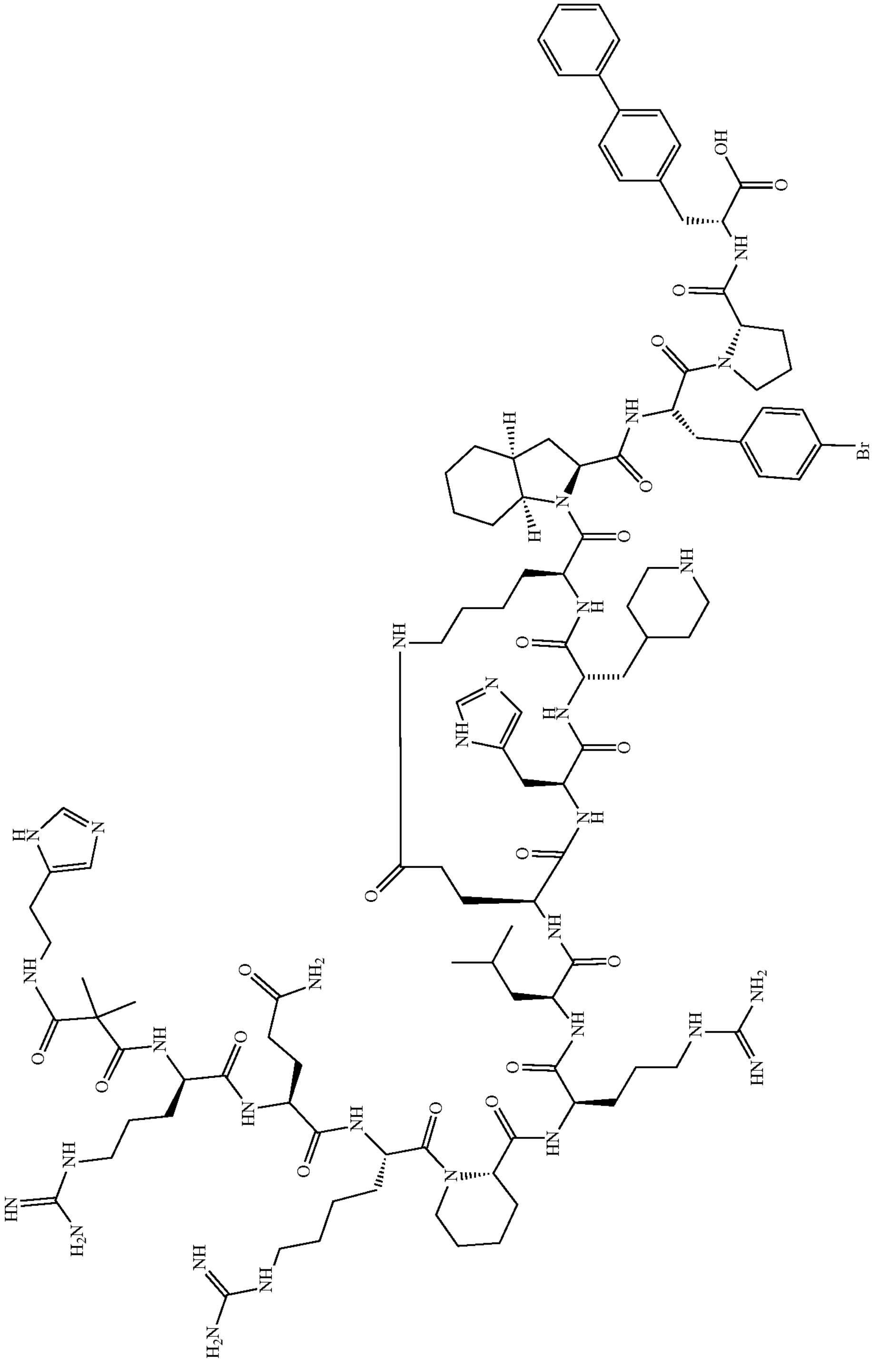

-continued
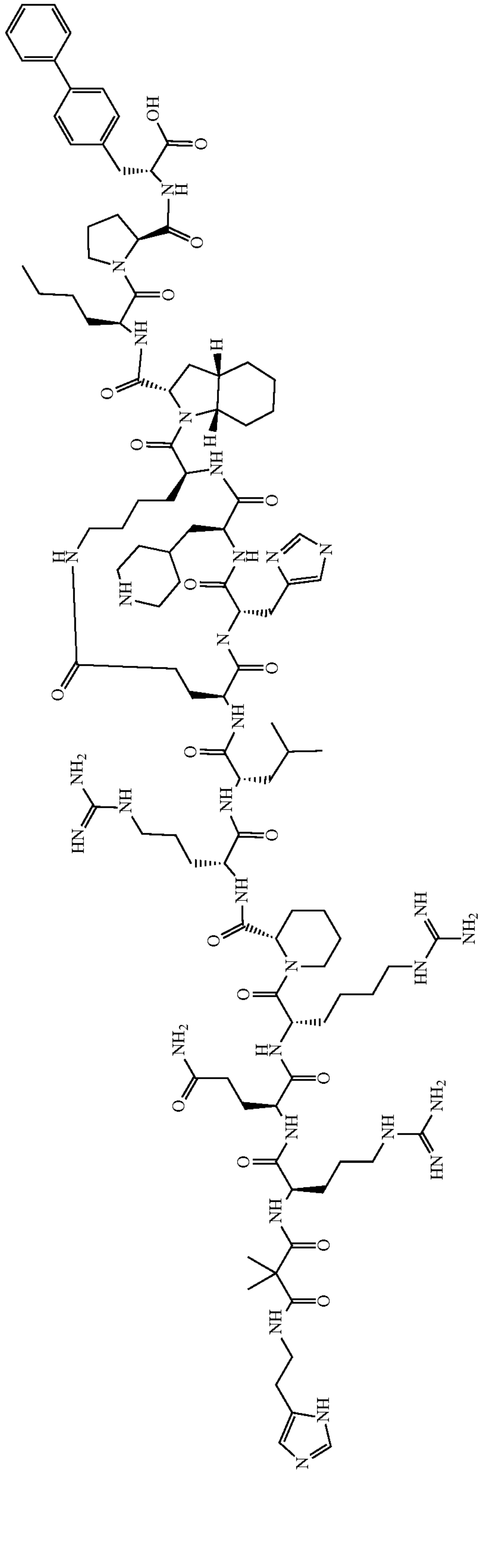
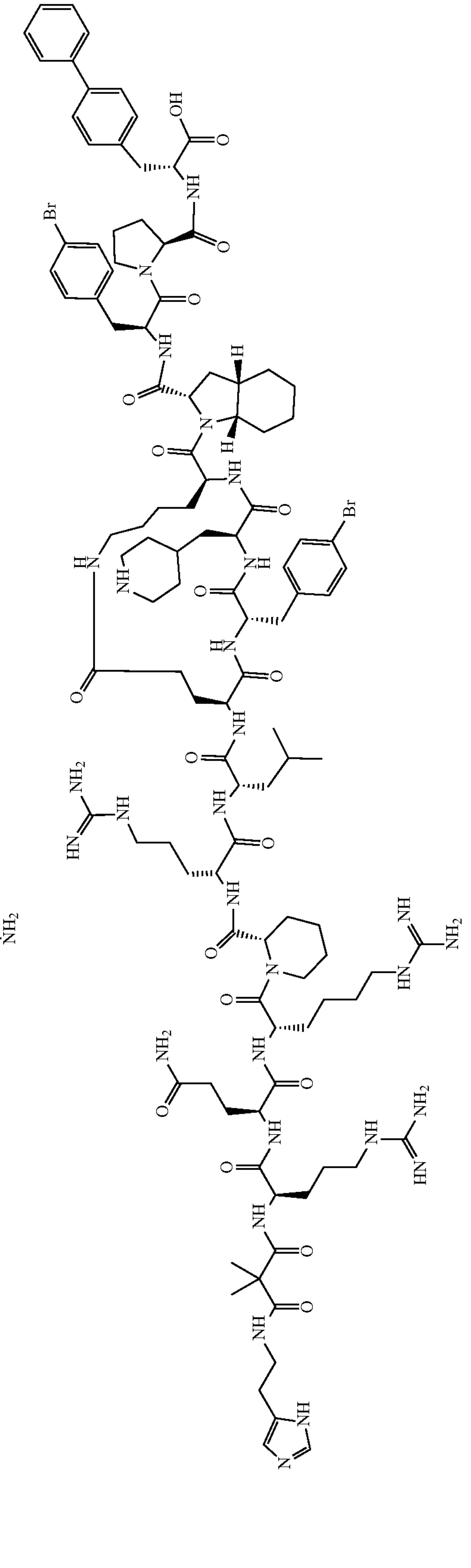

-continued
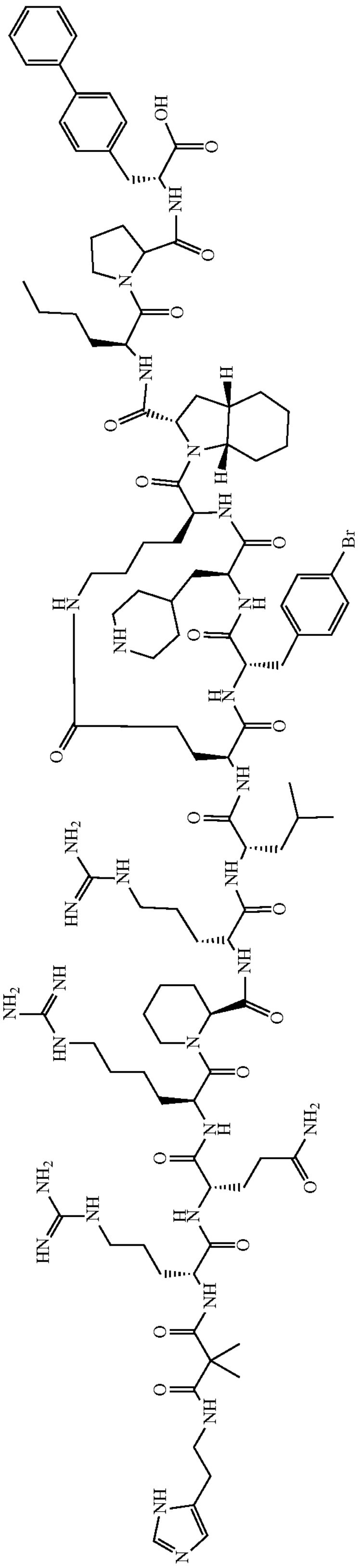
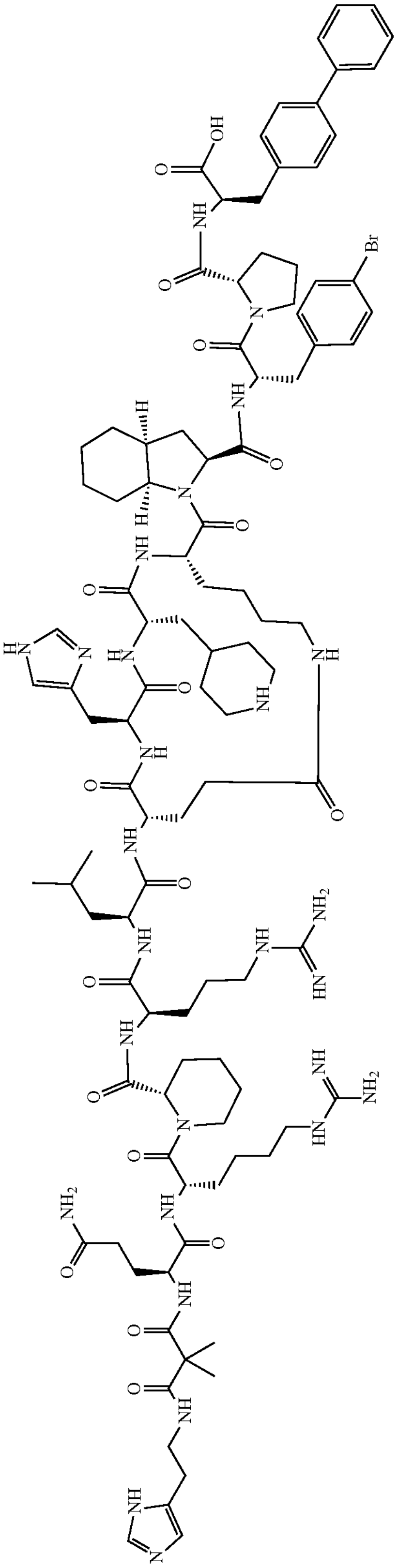

-continued
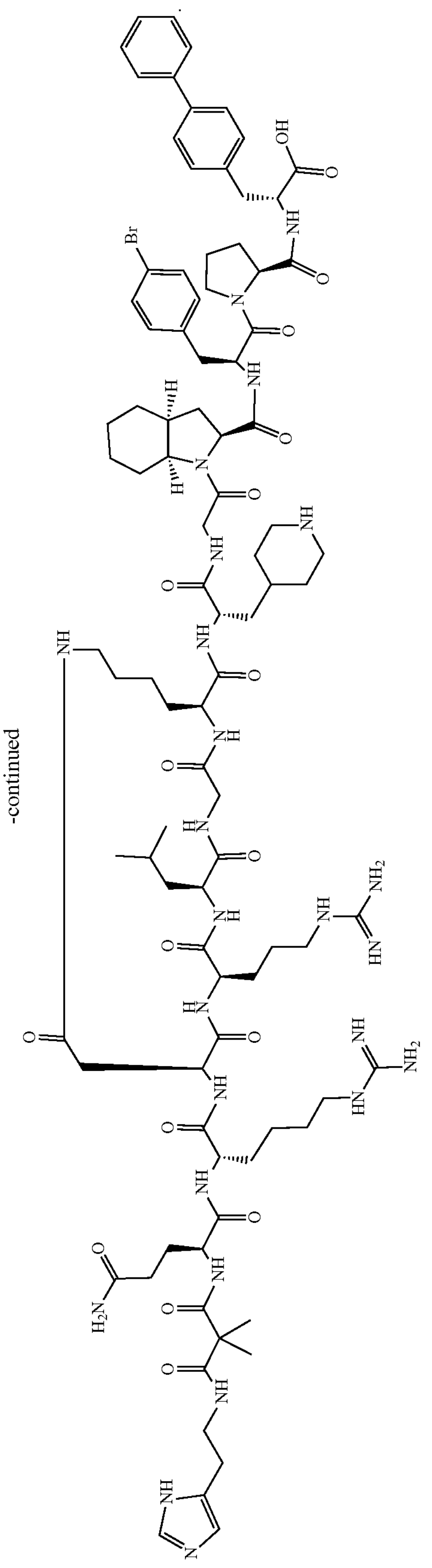

12. The compound according to claim 1 having apelin receptor agonist activity.

13. A pharmaceutical composition comprising a compound as defined in claim 1 and a pharmaceutically acceptable excipient.

14. The compound or composition according to claim 1 for use in medicine.

15. A method of agonizing human Apelin receptor in a patient in need thereof wherein the patient has at least one condition selected from the group consisting of: cardiovascular disease, acute decompensated heart failure, congestive heart failure, myocardial infarction, cardiomyopathy, ischemia, ischemia/reperfusion injury, diabetes, obesity, cancer, metastatic disease, fluid homeostasis, pathological angiogenesis, retinopathy, HIV infection, pulmonary arterial hypertension (PAH), pulmonary vessel hypertension, cardiac inflammation, reduced right heart ventricular function, kidney failure, hypertension, polycystic kidney disease, hyponatremia, syndrome of inappropriate antidiuretic hormone secretion (SIADH), peripheral arterial disease (PAD), acute coronary syndrome (ACS), stroke, atherosclerosis, diabetic nephropathy, neuropathy, non-alcoholic fatty liver disease, non-alcoholic steatosis, and portal hypertension, said method comprising administering a therapeutically effective amount of the compound according to claim 1 to the patient in need thereof.

16. The compound according to claim 2, wherein n is 2.

17. The compound according to claim 2, wherein $R^1$ and $R^2$ are independently selected from hydrogen or a $C_{1-6}$ alkyl group.

18. The compound according to claim 3, wherein $R^1$ and $R^2$ are independently selected from hydrogen or a $C_{1-6}$ alkyl group.

19. The compound according to claim 2, wherein X is -DArg-.

20. The compound according to claim 3, wherein X is -DArg-.

* * * * *

SEQUENCE LISTING

<160> NUMBER OF SEQ ID NOS: 7

<210> SEQ ID NO 1
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(1)
<223> OTHER INFORMATION: Imidazole amide capping group
<220> FEATURE:
<221> NAME/KEY: SITE
<222> LOCATION: (2)..(2)
<223> OTHER INFORMATION: D-Arg
<220> FEATURE:
<221> NAME/KEY: SITE
<222> LOCATION: (4)..(4)
<223> OTHER INFORMATION: homoArg
<220> FEATURE:
<221> NAME/KEY: SITE
<222> LOCATION: (5)..(5)
<223> OTHER INFORMATION: homoPro
<220> FEATURE:
<221> NAME/KEY: SITE
<222> LOCATION: (6)..(6)
<223> OTHER INFORMATION: D-Arg
<220> FEATURE:
<221> NAME/KEY: SITE
<222> LOCATION: (8)..(8)
<223> OTHER INFORMATION: Glu joined to Lys at position 11 via lactam bridge
<220> FEATURE:
<221> NAME/KEY: SITE
<222> LOCATION: (10)..(10)
<223> OTHER INFORMATION: Piperidinylalanine
<220> FEATURE:
<221> NAME/KEY: SITE
<222> LOCATION: (11)..(11)
<223> OTHER INFORMATION: Lys joined to Glu at position 8 via a lactam bridge
<220> FEATURE:
<221> NAME/KEY: SITE
<222> LOCATION: (12)..(12)
<223> OTHER INFORMATION: octahydroindole-2-carboxylic acid
<220> FEATURE:
<221> NAME/KEY: SITE
<222> LOCATION: (13)..(13)
<223> OTHER INFORMATION: 4-BrPhe
<220> FEATURE:
<221> NAME/KEY: SITE
<222> LOCATION: (15)..(15)
<223> OTHER INFORMATION: D-Biphenylalanine

<400> SEQUENCE: 1

```
Xaa Xaa Gln Xaa Xaa Xaa Leu Xaa His Xaa Xaa Xaa Xaa Pro Xaa
1               5                   10                  15
```

<210> SEQ ID NO 2
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(1)
<223> OTHER INFORMATION: Imidazole amide capping group
<220> FEATURE:
<221> NAME/KEY: SITE
<222> LOCATION: (2)..(2)
<223> OTHER INFORMATION: D-Arg
<220> FEATURE:
<221> NAME/KEY: SITE
<222> LOCATION: (4)..(4)

-continued

<223> OTHER INFORMATION: homoArg
<220> FEATURE:
<221> NAME/KEY: SITE
<222> LOCATION: (5)..(5)
<223> OTHER INFORMATION: homoPro
<220> FEATURE:
<221> NAME/KEY: SITE
<222> LOCATION: (6)..(6)
<223> OTHER INFORMATION: D-Arg
<220> FEATURE:
<221> NAME/KEY: SITE
<222> LOCATION: (8)..(8)
<223> OTHER INFORMATION: Glu joined to Lys at position 11 via lactam bridge
<220> FEATURE:
<221> NAME/KEY: SITE
<222> LOCATION: (10)..(10)
<223> OTHER INFORMATION: Piperidinylalanine
<220> FEATURE:
<221> NAME/KEY: SITE
<222> LOCATION: (11)..(11)
<223> OTHER INFORMATION: Lys joined to Glu at position 8 via a lactam bridge
<220> FEATURE:
<221> NAME/KEY: SITE
<222> LOCATION: (12)..(12)
<223> OTHER INFORMATION: octahydroindole-2-carboxylic acid
<220> FEATURE:
<221> NAME/KEY: SITE
<222> LOCATION: (13)..(13)
<223> OTHER INFORMATION: Nle
<220> FEATURE:
<221> NAME/KEY: SITE
<222> LOCATION: (15)..(15)
<223> OTHER INFORMATION: D-Biphenylalanine

<400> SEQUENCE: 2

```
Xaa Xaa Gln Xaa Xaa Xaa Leu Xaa His Xaa Xaa Xaa Xaa Pro Xaa
1               5                   10                  15
```

<210> SEQ ID NO 3
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(1)
<223> OTHER INFORMATION: Imidazole amide capping group
<220> FEATURE:
<221> NAME/KEY: SITE
<222> LOCATION: (2)..(2)
<223> OTHER INFORMATION: D-Arg
<220> FEATURE:
<221> NAME/KEY: SITE
<222> LOCATION: (4)..(4)
<223> OTHER INFORMATION: homoArg
<220> FEATURE:
<221> NAME/KEY: SITE
<222> LOCATION: (5)..(5)
<223> OTHER INFORMATION: homoPro
<220> FEATURE:
<221> NAME/KEY: SITE
<222> LOCATION: (6)..(6)
<223> OTHER INFORMATION: D-Arg
<220> FEATURE:
<221> NAME/KEY: SITE
<222> LOCATION: (8)..(8)
<223> OTHER INFORMATION: Glu joined to Lys at position 11 via lactam bridge
<220> FEATURE:
<221> NAME/KEY: SITE
<222> LOCATION: (9)..(9)
<223> OTHER INFORMATION: 4-BrPhe
<220> FEATURE:
<221> NAME/KEY: SITE -continued
<222> LOCATION: (10)..(10)
<223> OTHER INFORMATION: Piperidinylalanine
<220> FEATURE:
<221> NAME/KEY: SITE
<222> LOCATION: (11)..(11)
<223> OTHER INFORMATION: Lys joined to Glu at position 8 via a lactam bridge
<220> FEATURE:
<221> NAME/KEY: SITE
<222> LOCATION: (12)..(12)
<223> OTHER INFORMATION: octahydroindole-2-carboxylic acid
<220> FEATURE:
<221> NAME/KEY: SITE
<222> LOCATION: (13)..(13)
<223> OTHER INFORMATION: 4-BrPhe
<220> FEATURE:
<221> NAME/KEY: SITE
<222> LOCATION: (15)..(15)
<223> OTHER INFORMATION: D-Biphenylalanine

<400> SEQUENCE: 3

```
Xaa Xaa Gln Xaa Xaa Xaa Leu Xaa Xaa Xaa Xaa Xaa Xaa Pro Xaa
1               5                   10                  15
```

<210> SEQ ID NO 4
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(1)
<223> OTHER INFORMATION: Imidazole amide capping group
<220> FEATURE:
<221> NAME/KEY: SITE
<222> LOCATION: (2)..(2)
<223> OTHER INFORMATION: D-Arg
<220> FEATURE:
<221> NAME/KEY: SITE
<222> LOCATION: (4)..(4)
<223> OTHER INFORMATION: homoArg
<220> FEATURE:
<221> NAME/KEY: SITE
<222> LOCATION: (5)..(5)
<223> OTHER INFORMATION: homoPro
<220> FEATURE:
<221> NAME/KEY: SITE
<222> LOCATION: (6)..(6)
<223> OTHER INFORMATION: D-Arg
<220> FEATURE:
<221> NAME/KEY: SITE
<222> LOCATION: (8)..(8)
<223> OTHER INFORMATION: Glu joined to Lys at position 11 via lactam bridge
<220> FEATURE:
<221> NAME/KEY: SITE
<222> LOCATION: (9)..(9)
<223> OTHER INFORMATION: 4-BrPhe
<220> FEATURE:
<221> NAME/KEY: SITE
<222> LOCATION: (10)..(10)
<223> OTHER INFORMATION: Piperidinylalanine
<220> FEATURE:
<221> NAME/KEY: SITE
<222> LOCATION: (11)..(11)
<223> OTHER INFORMATION: Lys joined to Glu at position 8 via a lactam bridge
<220> FEATURE:
<221> NAME/KEY: SITE
<222> LOCATION: (12)..(12)
<223> OTHER INFORMATION: octahydroindole-2-carboxylic acid
<220> FEATURE:
<221> NAME/KEY: SITE
<222> LOCATION: (13)..(13)
<223> OTHER INFORMATION: Nle
<220> FEATURE:

<221> NAME/KEY: SITE
<222> LOCATION: (15)..(15)
<223> OTHER INFORMATION: D-Biphenylalanine

<400> SEQUENCE: 4

Xaa Xaa Gln Xaa Xaa Xaa Leu Xaa Xaa Xaa Xaa Xaa Xaa Pro Xaa
1               5                   10                  15

<210> SEQ ID NO 5
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(1)
<223> OTHER INFORMATION: Imidazole amide capping group
<220> FEATURE:
<221> NAME/KEY: SITE
<222> LOCATION: (3)..(3)
<223> OTHER INFORMATION: homoArg
<220> FEATURE:
<221> NAME/KEY: SITE
<222> LOCATION: (4)..(4)
<223> OTHER INFORMATION: homoPro
<220> FEATURE:
<221> NAME/KEY: SITE
<222> LOCATION: (5)..(5)
<223> OTHER INFORMATION: D-Arg
<220> FEATURE:
<221> NAME/KEY: SITE
<222> LOCATION: (7)..(7)
<223> OTHER INFORMATION: Glu joined to Lys at position 10 via lactam bridge
<220> FEATURE:
<221> NAME/KEY: SITE
<222> LOCATION: (9)..(9)
<223> OTHER INFORMATION: Piperidinylalanine
<220> FEATURE:
<221> NAME/KEY: SITE
<222> LOCATION: (10)..(10)
<223> OTHER INFORMATION: Lys joined to Glu at position 7 via a lactam bridge
<220> FEATURE:
<221> NAME/KEY: SITE
<222> LOCATION: (11)..(11)
<223> OTHER INFORMATION: octahydroindole-2-carboxylic acid
<220> FEATURE:
<221> NAME/KEY: SITE
<222> LOCATION: (12)..(12)
<223> OTHER INFORMATION: 4-BrPhe
<220> FEATURE:
<221> NAME/KEY: SITE
<222> LOCATION: (14)..(14)
<223> OTHER INFORMATION: D-Biphenylalanine

<400> SEQUENCE: 5

Xaa Gln Xaa Xaa Xaa Leu Xaa His Xaa Xaa Xaa Xaa Pro Xaa
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(1)
<223> OTHER INFORMATION: Imidazole amide capping group
<220> FEATURE:
<221> NAME/KEY: SITE
<222> LOCATION: (3)..(3)
<223> OTHER INFORMATION: homoArg -continued
<220> FEATURE:
<221> NAME/KEY: SITE
<222> LOCATION: (4)..(4)
<223> OTHER INFORMATION: Arg joined to Lys at position 8 via a lactam bridge
<220> FEATURE:
<221> NAME/KEY: SITE
<222> LOCATION: (5)..(5)
<223> OTHER INFORMATION: D-Arg
<220> FEATURE:
<221> NAME/KEY: SITE
<222> LOCATION: (8)..(8)
<223> OTHER INFORMATION: Lys joined to Arg at position 4 via a lactam bridge
<220> FEATURE:
<221> NAME/KEY: SITE
<222> LOCATION: (9)..(9)
<223> OTHER INFORMATION: Piperidinylalanine
<220> FEATURE:
<221> NAME/KEY: SITE
<222> LOCATION: (11)..(11)
<223> OTHER INFORMATION: octahydroindole-2-carboxylic acid
<220> FEATURE:
<221> NAME/KEY: SITE
<222> LOCATION: (12)..(12)
<223> OTHER INFORMATION: 4-BrPhe
<220> FEATURE:
<221> NAME/KEY: SITE
<222> LOCATION: (14)..(14)
<223> OTHER INFORMATION: D-Biphenylalanine

<400> SEQUENCE: 6

Xaa Gln Xaa Xaa Xaa Leu Gly Xaa Xaa Gly Xaa Xaa Pro Xaa
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(1)
<223> OTHER INFORMATION: Aryl amide capping group
<220> FEATURE:
<221> NAME/KEY: VARIANT
<222> LOCATION: (2)..(2)
<223> OTHER INFORMATION: D-Arg or absent
<220> FEATURE:
<221> NAME/KEY: SITE
<222> LOCATION: (4)..(4)
<223> OTHER INFORMATION: homoArg
<220> FEATURE:
<221> NAME/KEY: VARIANT
<222> LOCATION: (5)..(5)
<223> OTHER INFORMATION: may be homoPro; or may be Arg joined to Lys at position 9 via a lactam bridge
<220> FEATURE:
<221> NAME/KEY: SITE
<222> LOCATION: (6)..(6)
<223> OTHER INFORMATION: D-Arg
<220> FEATURE:
<221> NAME/KEY: VARIANT
<222> LOCATION: (8)..(8)
<223> OTHER INFORMATION: may be Gly; or may be Glu joined to Lys at position 11 via lactam bridge
<220> FEATURE:
<221> NAME/KEY: VARIANT
<222> LOCATION: (9)..(9)
<223> OTHER INFORMATION: may be His; or may be 4-BrPHe; or may be Lys joined to Arg at position 5 via a lactam bridge
<220> FEATURE:
<221> NAME/KEY: SITE
<222> LOCATION: (10)..(10)
<223> OTHER INFORMATION: Piperidinylalanine
<220> FEATURE:

-continued

```
<221> NAME/KEY: VARIANT
<222> LOCATION: (11)..(11)
<223> OTHER INFORMATION: may be Gly; or may be Lys joined to Glu at
      position 8 via a lactam bridge
<220> FEATURE:
<221> NAME/KEY: SITE
<222> LOCATION: (12)..(12)
<223> OTHER INFORMATION: octahydroindole-2-carboxylic acid
<220> FEATURE:
<221> NAME/KEY: VARIANT
<222> LOCATION: (13)..(13)
<223> OTHER INFORMATION: Nle or 4-BrPhe
<220> FEATURE:
<221> NAME/KEY: SITE
<222> LOCATION: (15)..(15)
<223> OTHER INFORMATION: D-Biphenylalanine

<400> SEQUENCE: 7

Xaa Xaa Gln Xaa Xaa Xaa Leu Xaa Xaa Xaa Xaa Xaa Xaa Pro Xaa
1               5                   10                  15
```